United States Patent
Toyonaga et al.

[11] Patent Number: 6,025,917
[45] Date of Patent: Feb. 15, 2000

[54] POLARIZATION CHARACTERISTIC MEASURING METHOD AND APPARATUS

[75] Inventors: Shuji Toyonaga; Masahisa Shiroshita; Takayuki Suga; Yoshitaro Nakano, all of Shizuoka, Japan

[73] Assignee: Laboratory of Molecular Biophotonics, Shizuoka, Japan

[21] Appl. No.: 09/068,087

[22] PCT Filed: Sep. 24, 1997

[86] PCT No.: PCT/JP97/03391

§ 371 Date: May 1, 1998

§ 102(e) Date: May 1, 1998

[87] PCT Pub. No.: WO98/13676

PCT Pub. Date: Apr. 2, 1998

[30] Foreign Application Priority Data

Sep. 24, 1996 [JP] Japan .................................. 8-251803

[51] Int. Cl.$^7$ ................... G01J 4/00; G02F 1/01; G02B 21/06
[52] U.S. Cl. ................... 356/364; 356/367; 356/369; 250/225; 359/385; 359/386
[58] Field of Search ...................... 356/364, 367, 356/369, 372, 300, 301; 250/225; 359/385, 386

[56] References Cited

U.S. PATENT DOCUMENTS

| | | | |
|---|---|---|---|
| 5,073,025 | 12/1991 | Brooks | 356/364 |
| 5,552,889 | 9/1996 | Meier | 356/364 |
| 5,764,363 | 6/1998 | Ooki et al. | 356/364 |

FOREIGN PATENT DOCUMENTS

| | | |
|---|---|---|
| 55-109949 | 8/1980 | Japan . |
| 57-84339 | 5/1982 | Japan . |
| 58-117439 | 7/1983 | Japan . |
| 59-182341 | 10/1984 | Japan . |
| 62-38363 | 2/1987 | Japan . |
| 1-209343 | 8/1989 | Japan . |
| 8-54340 | 2/1996 | Japan . |

OTHER PUBLICATIONS

Toyonaga et al.; "Detection of Minute Quantities of Substances in Organisms", vol. 26, No. 9, place & date of publication not known.

Axelrod, Daniel; "Carbocyanine Dye Orientation in Red Cell Membrane Studied by Microscopic Fluorescence Polarization", Biophysical Journal, vol. 26, Jun. 1979, pp. 557–573.

Dix et al.; "Mapping of fluorescence anisotrophy in living cells by ratio imaging"; Biophysical Journal, vol. 57, Feb. 1990, pp. 231–241.

(List continued on next page.)

*Primary Examiner*—Frank G. Font
*Assistant Examiner*—Roy M. Punnoose
*Attorney, Agent, or Firm*—Leydig, Voit & Mayer, Ltd.

[57] ABSTRACT

Provided is a polarization characteristic measuring method and apparatus for accurately measuring a polarization characteristic of fluorescence or Raman-scattered light emitted when a sample is exposed to light. The sample is exposed to excitation light radiated from a pulsed excitation light source and converted to p-polarized light by polarizer and half-wave plate, and photodetectors measure an intensity $I_{pp}$ of a p-polarized component and an intensity $I_{ps}$ of an s-polarized component of fluorescence emitted from the sample under irradiation with the excitation light. In similar fashion, the sample is exposed to the excitation light of s-polarized light and the detectors measure an intensity $I_{sp}$ of a p-polarized component and an intensity $I_{ss}$ of an s-polarized component of fluorescence emitted from the sample under irradiation. From these measured values, G factor is calculated according to the following equation:

$$G=[(I_{pp} \cdot I_{sp})/(I_{ps} \cdot I_{ss})]^{1/2}$$

and polarization response correction is effected based on this G factor to obtain the polarization characteristic of fluorescence.

17 Claims, 22 Drawing Sheets

OTHER PUBLICATIONS

Lakowicz et al.; "Time–Resolved Fluorescence.Intensity and Anisotropy Decays of 2,5–Diphenyloxazole by Two–Photon Excitation and Frequency–Domain Fluorometry", Journal of Physical Chemistry, vol. 96, No. 7, 1992, pp. 3000–3006.

Lakowicz et al.; "Anomalous differential polarized phase angles for two–photon excitation with isotropic depolarizing rotations" Chem. Phys. Letters, vol. 191, No. 1,2 Mar. 27, 1992, pp. 47–53.

Lakowicz et al.; "Anisotropy spectra of indole and N–acetyl–L–tryptophanamide observed for two–photon excitation of fluorescence", Chemical Physics Letters, vol. 194, No. 4,5,6, Jul. 3, 1992, pp. 282–287.

Lakowicz et al.; "Tryptophan fluorescence intensity and anisotrophy decays of human serum albumin resulting from one–photon and two–photon exictation"; Biophys, Chem. 45 (1992) pp. 1–6.

Lakowicz et al.; "Characterization of p–bis(O–methylstyryl) benzene as a lifetime and anisotropy decay standard for two–photon induced fluorescence", Biophysical Chemistry, 47 (1993), pp. 1–7.

Suzuki et al.; "Spatiotemporal Relationships Among Early Events of Fertilization in Sea Urchin Eggs Revealed by Multiview Microscopy", Biophysical Journal, vol. 68, Mar. 1995, pp. 739–748.

INTENSITY DECAYS OF POLARIZED COMPONENTS
OF FLUORESCENCE FROM FLUORESCENT
MOLECULES HAVING ROTATIONAL CORRELATION
TIME OF $\theta_1$ INTENSITY DECAYS OF POLARIZED COMPONENTS
OF FLUORESCENCE FROM FLUORESCENT
MOLECULES HAVING ROTATIONAL CORRELATION
TIME OF $\theta_2$

DECAYS OF POLARIZATION CHARACTERISTIC P1

DECAYS OF POLARIZATION CHARACTERISTIC P2

DECAYS OF POLARIZATION
CHARACTERISTIC P3

DECAYS OF POLARIZATION
CHARACTERISTIC P4

FITC-LABELED OLIGONUCLEOTIDE UNDER MICROSCOPE
WITHOUT DETECTING-SIDE POLARIZER

FITC-LABELED OLIGONUCLEOTIDE UNDER MICROSCOPE
WITH DETECTING-SIDE POLARIZER

ANISOTROPY DECAYS OF FITC-LABELED OLIGONUCLEOTIDE UNDER MICROSCORE

ANISOTROPY DECAYS OF FITC-LABELED OLIGONUCLEOTIDE

INTENSITY DECAYS OF FLUORESCENCE OF HDAF SOLUTION

INTENSITY DECAYS OF FLUORESCENCE OF HDAF-STAINED NG CELL

ANISOTROPY DECAYS

SCHEMATIC DIAGRAM OF SAMPLE IN WHICH
FREE FLUORESCENT PROBE(HDAF SOLUTION)
AND FLUORESCENT PROBE BOUND TO TARGET
(HDAF-STAINED NG CELL) COEXIST

PROBE MOLECULES
CAPTURED BY CELL MEMBRANE

PROBE MOLECULES FLOATING
IN MICELLE FORM

Fig.19

VALUES OF ANISOTROPY RATIO $P_2$ IN FREE PROBE
REGION AND IN BOUND PROBE REGION, AND
CONTRAST BETWEEN THEM

|  |  | ANISOTROPY RATIO $P_2$ | | | |
|---|---|---|---|---|---|
|  |  | DC MEASUREMENT | | TIME-RESOLVED MEASUREMENT | |
|  |  | MEAN | STANDARD DEVIATION | MEAN | STANDARD DEVIATION |
| REGIONS | FREE REGION | 0.044 | 0.003 | 0.016 | 0.004 |
| | BOUND REGION | 0.086 | 0.007 | 0.069 | 0.012 |
| CONTRAST | | 0.32 | | 0.62 | |

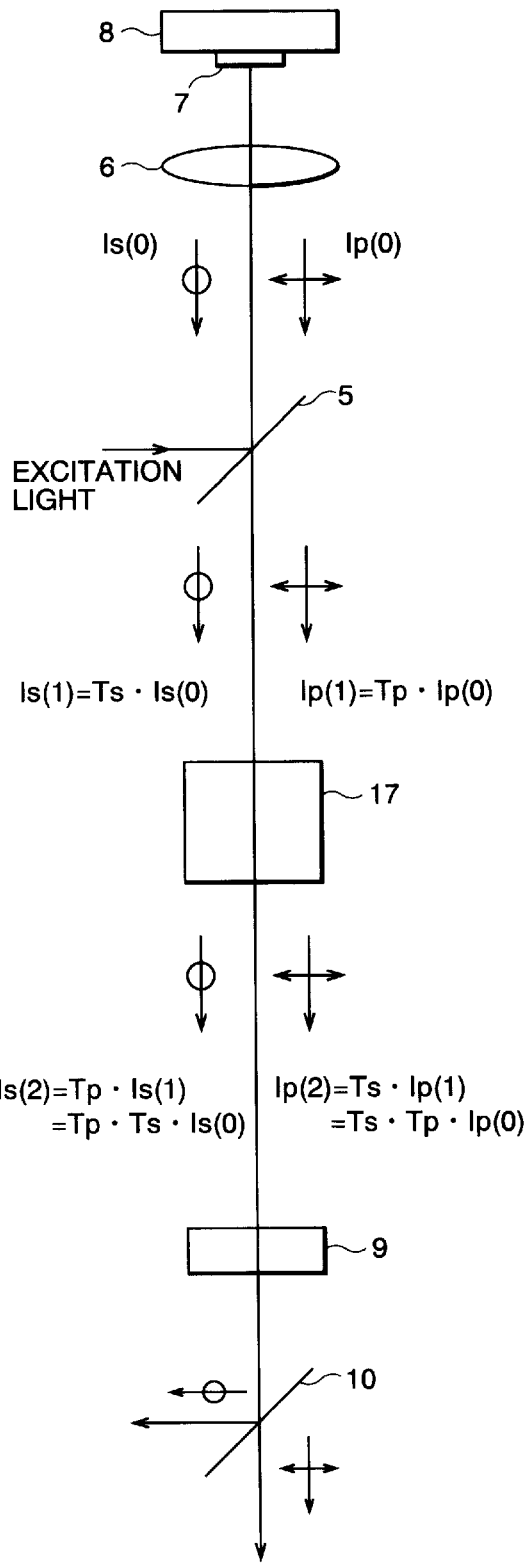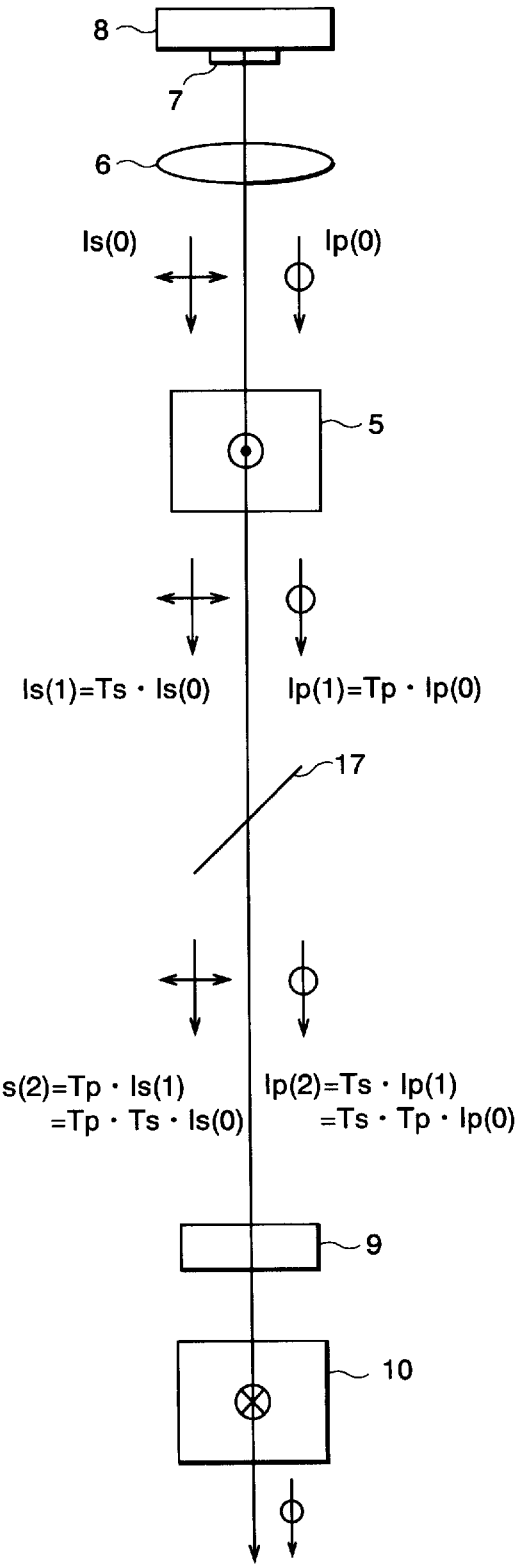

SELECTIVE EXCITATION BY ONE-PHOTON EXCITATION
AND TWO-PHOTON EXCITATION

CHANGE OF ANISOTROPY RATIO OF FLUORESCENCE
(EXCITATION WITH STEADY-STATE LIGHT)

SENSITIVITY OF ANISOTROPY RATIO OF FLUORESCENCE
(EXCITATION WITH STEADY-STATE LIGHT)

Fig.25

| Glycerol % | MEAN ANISOTROPY RATIO $P_2$ | | STANDARD DEVIATION $\sigma$ | |
|---|---|---|---|---|
| | ONE-PHOTON EXCITATION | TWO-PHOTON EXCITATION | ONE-PHOTON EXCITATION | TWO-PHOTON EXCITATION |
| 50 | 0.021 | 0.024 | 0.003 | 0.003 |
| 60 | 0.034 | 0.041 | 0.003 | 0.003 |
| 70 | 0.054 | 0.076 | 0.004 | 0.004 |
| 80 | 0.091 | 0.127 | 0.005 | 0.004 |
| 90 | 0.190 | 0.248 | 0.009 | 0.006 |

Fig.27

| Glycerol % | $\Delta P_2$ [/10%] ||
| --- | --- | --- |
| | ONE-PHOTON EXCITATION | TWO-PHOTON EXCITATION |
| 50 | 0.014 | 0.017 |
| 60 | 0.019 | 0.035 |
| 70 | 0.037 | 0.051 |
| 80 | 0.099 | 0.121 |
| 90 | | |

*Fig.29*

| Glycerol % | $P_2/\sigma$ | | $\Delta P_2/\sigma$ | |
|---|---|---|---|---|
| | ONE-PHOTON EXCITATION | TWO-PHOTON EXCITATION | ONE-PHOTON EXCITATION | TWO-PHOTON EXCITATION |
| 50 | 7 | 8 | 5 | 6 |
| 60 | 10 | 13 | 6 | 11 |
| 70 | 13 | 21 | 9 | 14 |
| 80 | 17 | 30 | 19 | 29 |
| 90 | 22 | 45 | | |

POLARIZATION CHARACTERISTIC MEASURING METHOD AND APPARATUS

TECHNICAL FIELD

This invention relates to a polarization characteristic measuring apparatus and method for measuring a characteristic of polarization of fluorescence or Raman-scattered light appearing when a sample is exposed to light.

BACKGROUND ART

When a sample is exposed to light, light of the same wavelength as that of the illuminating light appears in the form of reflected light and scattered light and, in addition thereto, there are cases where light of wavelengths different from that of the illuminating light is emergent (for example, fluorescence and Raman-scattered light). Useful information about the sample can be obtained by measuring the intensity of this fluorescence or Raman-scattered light, and useful information about the sample can also be obtained by measuring the characteristic of polarization of these beams.

For example, when a sample containing a fluorescent probe is exposed to excitation light and when depolarization of fluorescence emitted from the sample is measured, we can know whether there exists the fluorescent probe bound to a target. More specifically, when the sample containing the fluorescent probe is excited with linearly polarized pulsed light, fluorescence is emitted from the fluorescent probe. The polarization state of the fluorescence is almost linearly polarized at the beginning of exposure to the excitation light; but irregular rotation of the fluorescent probe because of the Brownian motion will disturb the molecular axes of excited fluorescent probe molecules, so that the fluorescence will become gradually depolarized with a lapse of time and a unpolarized state will result finally. The rate of this depolarization of the free fluorescent probe is different from that of the fluorescent probe bound to the target and, therefore, we can know whether the fluorescent probe bound to the target is present, by making use of the difference in the rate of depolarization.

Accordingly, if a two-dimensional image of degrees of this fluorescence depolarization can be measured under a microscope, a location of the fluorescent probe bound to the target can be specified and the behavior or the like of the target in the sample can be analyzed; it is, therefore, expected that this method can contribute to elucidation of various functions in cells, for example. Similarly, it is also expected that useful information concerning the sample can be obtained by measurement of a two-dimensional image of polarization characteristic of the Raman-scattered light under the microscope.

Incidentally, the technique for observing the two-dimensional image of the polarization state of fluorescence is described in D. Axelrod, "Carbocyanine Dye Orientation in Red Cell Membrane studied by Microscopic Fluorescence Polarization," Biophys. J., Vol. 26, pp. 557–574 (1979) and K. Suzuki et al., "Spatiotemporal Relationships Among Early Events of Fertilization in Sea Urchin Eggs Revealed by Multiview Microscopy," Biophys. J., Vol. 68, pp. 739–748 (1995).

The technique described in the paper of D. Axelrod concerns the method for measuring states of polarization of fluorescence generated under irradiation of steady-state light (linearly polarized excitation light), under the microscope and thereby analyzing orientation and mobility of fluorescent dye in a biomembrane. A photodetector used herein is a photomultiplier tube, which obtains a two-dimensional image of fluorescence polarization by scanning the diaphragm on the fluorescent image plane. A problem arising in measuring such fluorescence polarization is measurement errors caused by different responses of the photodetector and the optical system except for the polarizing device to different directions of polarization. In the technique described in this paper, the measurement errors are corrected (polarization response correction) by allowing fairly unpolarized light to pass through a light detecting optical system (an optical system from the sample to the photodetector) and the photodetector.

The technique described in the paper of K. Suzuki concerns the method for splitting the fluorescence emitted from the sample into mutually orthogonal components of linearly polarized light by a polarizing beam splitter, picking up each of images of the two split fluorescent beams by a single camera, and thereby analyzing stationary molecular orientation of the sample. In the technique described in this paper, the polarization response correction is effected by making use of the fact that when a homogeneous sample is excited by unpolarized excitation light, the fluorescence emitted from the sample is of no polarization at all.

However, the techniques described in the paper of D. Axelrod and in the paper of K. Suzuki employ the polarization response correction using the unpolarized light, and the accuracy of correction is low, because this unpolarized light is different from the fluorescence to be observed originally; the measurement accuracy of polarization characteristic is also low accordingly. It is not easy to make ideally unpolarized light.

The present invention has been accomplished in order to solve the above problem and an object of the invention is to provide a polarization characteristic measuring method and apparatus that can measure a characteristic of polarization of a second beam (fluorescence or Raman-scattered light) emitted from a sample irradiated by a first beam (excitation light or illuminating light), with accuracy.

SUMMARY OF INVENTION

A polarization characteristic measuring method according to the present invention is a polarization characteristic measuring method using beam splitting means for reflecting one of a first beam for irradiation of a sample and a second beam emitted from the sample and for transmitting the other, the polarization characteristic measuring method being adapted for guiding the first beam via the beam splitting means onto the sample, thereby effecting irradiation of the sample, and for measuring a polarization characteristic of the second beam emitted from the sample under the irradiation and traveling via the beam splitting means, the polarization characteristic measuring method comprising: (1) a first step of measuring an intensity $I_{pp}$ of a p-polarized component and an intensity $I_{pa}$ of an s-polarized component of the second beam emitted when the sample is irradiated with said first beam in the form of p-polarized light with respect to the beam splitting means; (2) a second step of measuring an intensity $I_{sp}$ of a p-polarized component and an intensity $I_{ss}$ of an s-polarized component of the second beam emerging when the sample is irradiated with said first beam in the form of s-polarized light with respect to the beam splitting means; (3) a third step of calculating a polarization response correction factor G according to the following equation:

$$G = [(I_{pp} \cdot I_{sp})/(I_{ps} \cdot I_{ss})]^{1/2}; \text{ and}$$

(4) a fourth step of performing polarization response correction based on the polarization response correction factor G to obtain the polarization characteristic of the second beam.

According to this polarization characteristic measuring method, in the first step the first beam is changed to the p-polarized light with respect to the beam splitting means to irradiate the sample therewith and the intensity $I_{pp}$ of the p-polarized component and the intensity $I_{ps}$ of the s-polarized component of the second beam emitted from the sample under the irradiation are measured; and in the second step the first beam is changed to the s-polarized light with respect to the beam splitting means to irradiate the sample therewith and the intensity $I_{sp}$ of the p-polarized component and the intensity $I_{ss}$ of the s-polarized component of the second beam emitted from the sample under the irradiation are measured. Then, in the third step the polarization response correction factor G is calculated according to the above-stated equation and in the fourth step the polarization response correction is effected based on this polarization response correction factor G, thus obtaining the polarization characteristic of the second beam.

In the polarization characteristic measuring method according to the present invention, the second step comprises a step of radiating the first beam toward the sample set in the same location as during measurement of the first step. In this case, the polarization characteristic of the second beam is measured in a system in which a substance to emit the second beam is oriented at random in a sample.

In the polarization characteristic measuring method according to the present invention, the first step comprises a step of radiating the first beam toward the sample located at a position making a predetermined rotation angle about a center axis on a predetermined direction, and the second step comprises a step of radiating the first beam toward the sample located at a position making a rotation angle 90° different from the position of the predetermined rotation angle about the center axis. In this case, the polarization characteristic of the second beam is measured in a system in which a substance to emit the second beam is oriented along a fixed direction in a sample.

The polarization characteristic measuring method according to the present invention may be adapted as follows;

in the fourth step, the polarization characteristic of the second beam is calculated according to either equation below:

$$P_1(p)=(I_{pp}-G\cdot I_{ps})/(I_{pp}+G\cdot I_{ps}); \text{ or}$$

$$P_1(s)=(G\cdot I_{ss}-I_{sp})/(G\cdot I_{ss}+I_{sp});$$

the polarization characteristic is calculated according to either equation below:

$$P_2(p)=(I_{pp}-G\cdot I_{ps})/(I_{pp}+2\cdot G\cdot I_{ps}); \text{ or}$$

$$P_2(s)=(G\cdot I_{ss}-I_{sp})/(G\cdot I_{ss}+2\cdot I_{sp});$$

the polarization characteristic is calculated according to either equation below:

$$P_3(p)=1-G\cdot(I_{ps}/I_{pp}); \text{ or}$$

$$P_3(s)=G-(I_{sp}/I_{ss});$$

the polarization characteristic is calculated according to either equation below:

$$P_4(p)=(I_{pp}/I_{ps})-G; \text{ or}$$

$$P_4(s)=G\cdot(I_{ss}/I_{sp})=1.$$

Either one of them is a parameter suitable for representing the polarization characteristic of the second beam. Particularly, $P_3$ and $P_4$ can be calculated with less computational complexity.

In the polarization characteristic measuring method according to the present invention, the first beam is a beam of a wavelength that can undergo multiple photon absorption by the sample and the second beam is a beam emitted on the occasion of the multiple photon absorption. In this case, the polarization characteristic of the second beam is measured with high sensitivity and a high S/N ratio.

A polarization characteristic measuring apparatus according to the present invention is a polarization characteristic measuring apparatus using beam splitting means for reflecting one of a first beam for irradiation of a sample and a second beam emitted from the sample and for transmitting the other, the polarization characteristic measuring apparatus being adapted for guiding the first beam via the beam splitting means onto the sample, thereby effecting irradiation of the sample, and for measuring a polarization characteristic of the second beam emitted from the sample under the irradiation and traveling via the beam splitting means, the polarization characteristic measuring apparatus comprising: (1) a light source portion for outputting the first beam of linear polarized light for irradiation of the sample; (2) polarized direction rotating means for rotating a polarized direction of the first beam outputted from the light source portion; (3) detecting means for detecting intensities of respective p-polarized component and s-polarized component of the second beam traveling via the beam splitting means, out of beams emitted when the sample is irradiated with said first beam; (4) correction factor calculating means for calculating a polarization response correction factor G according to the following equation:

$$G=[(I_{pp}\cdot I_{sp})/(I_{ps}\cdot I_{ss})]^{1/2},$$

based on an intensity $I_{pp}$ of a p-polarized component and an intensity $I_{ps}$ of an s-polarized component of the second beam detected by the detecting means when the sample is irradiated with the first beam changed to p-polarized light with respect to the beam splitting means by the polarized direction rotating means and on an intensity $I_{sp}$ of a p-polarized component and an intensity $I_{ss}$ of an s-polarized component of the second beam detected by the detecting means when the sample is irradiated with the first beam changed to s-polarized light with respect to the beam splitting means by the polarized direction rotating means; and (5) polarization characteristic calculating means for performing polarization response correction based on the polarization response correction factor G to obtain a polarization characteristic of the second beam.

With this polarization characteristic measuring apparatus, the first beam of linearly polarized light for irradiation of the sample is outputted from the light source portion, the polarized direction of the first beam is rotated by the polarized direction rotating means, and the beam travels via the beam splitting means onto the sample. The detecting means detects the intensities of the respective p-polarized component and s-polarized component of the second beam traveling via the beam splitting means, out of beams emitted when the sample is irradiated with the first beam. Then the correction factor calculating means calculates the polarization response correction factor G according to the above-stated equation, based on the intensity $I_{pp}$ of the p-polarized component and the intensity $I_{ps}$ of the s-polarized component of the second beam detected by the detecting means when the sample is irradiated with the first beam changed to the p-polarized light with respect to the beam splitting means by the polarized direction rotating means and on the intensity $I_{sp}$ of the p-polarized component and the intensity $I_{ss}$ of the s-polarized component of the second beam detected by the detecting means when the sample is irradiated with the first beam changed to the s-polarized light with respect to the beam splitting means by the polarized direction rotating means; and the polarization characteristic calculating means performs the polarization response correction based on the polarization response correction factor G to obtain the polarization characteristic of the second beam.

In the polarization characteristic measuring apparatus according to the present invention, the correction factor calculating means calculates the polarization response correction factor G, based on the intensities $I_{pp}$, $I_{ps}$, $I_{sp}$, and $I_{ss}$ detected by the detecting means, for the sample located in a fixed location. In this case, the polarization characteristic of the second beam is measured in a system in which a substance to emit the second beam is oriented at random in a sample.

The polarization characteristic measuring apparatus according to the present invention further comprises sample rotating means for rotating the sample about a center axis on a predetermined direction, and the correction factor calculating means calculates the polarization response correction factor G, based on the intensities $I_{pp}$ and $I_{ps}$ detected by the detecting means, for the sample located at a position making a predetermined rotation angle about the center axis and on the intensities $I_{sp}$ and $I_{ss}$ detected by the detecting means, for the sample set at a position making a rotation angle 90° different from the position of the predetermined rotation angle about the center axis by the sample rotating means. In this case, the polarization characteristic of the second beam is measured in a system in which a substance to emit the second beam is oriented in a fixed direction in a sample.

In the polarization characteristic measuring apparatus according to the present invention, the polarization characteristic calculating means may calculate the polarization characteristic P of the second beam according to either equation below:

$$P_1(p) = (I_{pp} - G \cdot I_{ps})/(I_{pp} + G \cdot I_{ps}); \text{ or}$$

$$P_1(s) = (G \cdot I_{ss} - I_{sp})/(G \cdot I_{ss} + I_{sp});$$

the polarization characteristic calculating means may calculate the polarization characteristic of the second beam according to either equation below:

$$P_2(p) = (I_{pp} - G \cdot I_{ps})/(I_{pp} + 2 \cdot G \cdot I_{ps}); \text{ or}$$

$$P_2(s) = (G \cdot I_{ss} - I_{sp})/(G \cdot I_{ss} + 2 \cdot I_{sp});$$

the polarization characteristic calculating means may calculate the polarization characteristic of the second beam according to either equation below:

$$P_3(p) = 1 - G \cdot (I_{ps}/I_{pp}); \text{ or}$$

$$P_3(s) = G - (I_{sp}/I_{ss});$$

the polarization characteristic calculating means may calculate the polarization characteristic of the second beam according to either equation below:

$$P_4(p) = (I_{pp}/I_{ps}) - G; \text{ or}$$

$$P_4(s) = G \cdot (I_{ss}/I_{sp}) - 1.$$

Either one of them is a parameter suitable for representing the polarization characteristic of the second beam. Particularly, $P_3$ and $P_4$ can be calculated with less computational complexity.

In the polarization characteristic measuring apparatus according to the present invention, the light source portion outputs as the first beam a beam of a wavelength that can undergo multiple photon absorption by the sample, and the detecting means detects as the second beam a beam emitted on the occasion of the multiple photon absorption. In this case, the polarization characteristic of the second beam is measured with high sensitivity and a high S/N ratio.

Another polarization characteristic measuring apparatus according to the present invention is a polarization characteristic measuring apparatus comprising: (1) a light source portion for outputting a first beam for irradiation of a sample; (2) first beam splitting means for guiding the first bean onto the sample to effect irradiation of the sample and receiving a second beam emitted from the sample under the irradiation, the first beam splitting means reflecting one of the first beam and the second beam but transmitting the other; (3) second beam splitting means having a spectral characteristic equal to that of the first beam splitting means, the second beam splitting means having an plane of incidence 90° different from an plane of incidence of the first beam splitting means for the second beam, the second beam splitting means receiving the second beam outputted from the first beam splitting means; (4) detecting means for detecting intensities of respective p-polarized component and s-polarized component of the second beam traveling via the second beam splitting means; and (5) polarization characteristic calculating means for measuring a polarized characteristic of the second beam, based on the intensities of the respective p-polarized component and s-polarization component of the second beam detected by the detecting means.

With this polarization characteristic measuring apparatus, the first beam for irradiation of the sample is outputted from the light source portion and is guided via the first beam splitting means onto the sample. The second beam emitted when the sample is irradiated with the first beam travels successively via the first and second beam splitting means and the intensities of the respective p-polarized component and s-polarized component thereof are detected by the detecting means. Then the polarization characteristic is measured based on these intensities. Here, the first and second beam splitting means have the mutually identical spectral characteristics and also have the plane of incidence 90° shifted from each other with respect to the second beam; therefore, the spectral characteristics of the respective first and second beam splitting means cancel each other, thereby eliminating a measurement error of polarization characteristic caused thereby.

BRIEF DESCRIPTION OF DRAWINGS

FIG. 19 is a table to show values of anisotropy ratio $P_2$ of free probe region and bound probe region and contrast between them.

FIG. 20A and FIG. 20B are structural drawings of a fluorescence detecting optical system of the polarization characteristic measuring apparatus, which can also be suitably applicable to the case of multiphoton excitation, and are views observed along two orthogonal directions perpendicular to the optic axis of the fluorescence detecting optical system.

FIG. 25 is a table to show measured values of anisotropy ratio $P_2$ of fluorescence and standard deviation a against glycerol percentage, for each of the one-photon excitation case and the two-photon excitation case.

FIG. 27 is a table to show values of increment $\Delta P_2$ of anisotropy ratio $P_2$ of fluorescence against 10%-interval increase of glycerol percentage, for each of the one-photon excitation case and the two-photon excitation case.

FIG. 29 is a table to show values ($P_2/\sigma$) obtained by dividing the anisotropy ratio $P_2$ of fluorescence by the standard deviation a and values ($\Delta P_2/\sigma$) obtained by dividing the increment $\Delta P_2$ of the anisotropy ratio $P_2$ of fluorescence by the standard deviation $\sigma$, against glycerol percentage, for each of the one-photon excitation case and the two-photon excitation case.

BEST MODE FOR CARRYING OUT THE INVENTION

Embodiments of the present invention will be described in detail by reference to the appended drawings. In the explanation of the drawings the same elements will be denoted by the same reference symbols and redundant description will be omitted. Although the invention will be described as to the measurement of polarization characteristic of fluorescence, the invention is also applicable similarly to the measurement of polarization characteristic of Raman-scattered light. The term "polarization characteristic" generally means $P_1$, $P_2$, $P_3$, and $P_4$ defined below.

First, the polarization response correction will be described generally prior to the description of the polarization characteristic measuring method and apparatus according to the present invention. One of significant factors for the measurement errors on the occasion of measurement of polarization characteristic is polarization characteristics of the receiving optical system (the optical system from the sample to the photodetector) and the photodetector. The photodetector and the receiving optical system except for the polarizing device should equally respond to different polarization states ideally, but they demonstrate different responses depending upon directions of polarization in practice. Therefore, the polarization responses need to be corrected in order to obtain the true polarization characteristic of fluorescence.

Figure 1:
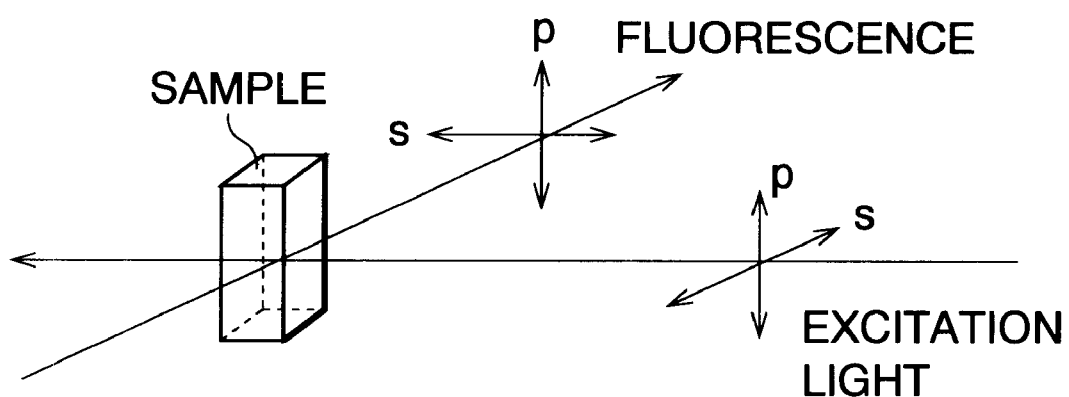
FIG. 1 is an explanatory drawing to illustrate how to obtain a G factor in measurement of polarization characteristic of dimension 0 (point).

An amount of this correction for the polarization responses is normally called G factor (polarization response correction factor) and is defined as follows in measurement of polarization characteristic of dimension 0 (point). FIG. 1 is an explanatory drawing to illustrate how to obtain the G factor in the measurement of polarization characteristic of dimension 0 (point). Linearly polarized excitation light in the p-polarization direction is allowed to enter the sample and to generate fluorescence. The fluorescence is measured as to linearly polarized components in the p-polarization direction (the direction parallel to the p-polarization direction of the excitation light) and in the s-polarization direction (the direction perpendicular to the p-polarization direction of the excitation light) by use of a polarizer, along a direction perpendicular to the direction of incidence of the excitation light, and intensities of the respective components are denoted by $I_{pp}$ and $I_{ps}$. Polarization degree $P_1$ (which is normally expressed by p) is defined as a parameter featuring a polarization characteristic of the fluorescence by the following equation.

$$P_1(p) = \frac{I_{pp} - I_{ps}}{I_{pp} + I_{ps}} \quad (1)$$

Further, anisotropy ratio $P_2$ (which is normally expressed by r) is defined by the following equation.

$$P_2(p) = \frac{I_{pp} - I_{ps}}{I_{pp} + 2I_{ps}} \quad (2)$$

Since intensities of fluorescence measured in practice are obtained through the receiving optical system and photodetector, they reflect the anisotropy thereof. Namely, letting $T_p$ be a response of the receiving optical system and photodetector to p-polarized light and $T_s$ be a response thereof to the s-polarized light, each of fluorescence intensities $I_{pp}'$ and $I_{ps}'$ measured in practice has the following relation with each of the true fluorescence intensities $I_{pp}$ and $I_{ps}$.

$$I_{pp}' = T_p \cdot I_{pp}, \; I_{ps}' = T_s \cdot I_{ps} \quad (3)$$

By substituting Eq. (3) into each of Eq. (1) and Eq. (2), relations of the polarization degree $P_1$ and anisotropy ratio $P_2$ each with the measured fluorescence intensities $I_{pp}'$, $I_{ps}'$ are expressed by the following equations.

$$P_1(p) = \frac{I_{pp}' - G \cdot I_{ps}'}{I_{pp}' + G \cdot I_{ps}'} \quad (4)$$

$$P_2(p) = \frac{I_{pp}' - G \cdot I_{ps}'}{I_{pp}' + 2G \cdot I_{ps}'} \quad (5)$$

Here, G appearing in each of Eq. (4) and Eq. (5) is a polarization response correction factor called G factor and is expressed by a ratio of the response $T_p$ to the p-polarized light to the response $T_s$ to the s-polarized light as follows.

$$G = \frac{T_p}{T_s} \quad (6)$$

This G factor is obtained as follows. The sample is irradiated by the s-polarized excitation light and the linearly polarized components of p-polarization and s-polarization of the fluorescence emitted are measured. Intensities of the respective components are denoted by $I_{sp}'$ and $I_{ss}'$. These have the following relations, similar to Eq. (3), with each of the true fluorescence intensities $I_{sp}$ and $I_{ss}$.

$$I_{sp}' = T_p \cdot I_{sp}, \; I_{ss}' = T_s \cdot I_{ss} \quad (7)$$

Since the intensity $I_{sp}$ of the p-polarized component of the fluorescence emitted by the s-polarized excitation light is considered to be equal to the intensity $I_{ss}$ of the s-polarized component, the following equation is obtained from Eq. (7).

$$\frac{T_p}{T_s} = \frac{I_{sp}'}{I_{ss}'} \quad (8)$$

Hence, the G factor expressed by Eq. (6) can be calculated from the following equation using the measured fluorescence intensities $I_{sp}'$ and $I_{ss}'$.

$$G = \frac{I_{sp}'}{I_{ss}'} \quad (9)$$

Namely, the polarization degree $P_1$ and anisotropy ratio $P_2$ can be obtained with high accuracy by effecting the polarization response correction using this G factor.

Figure 2:
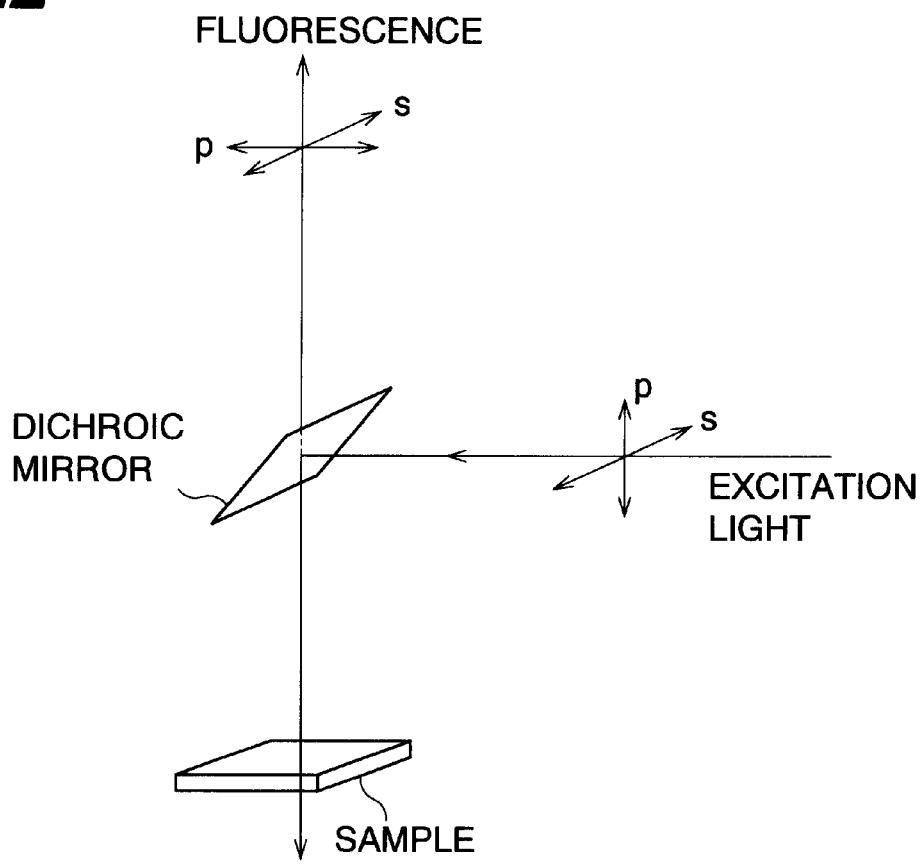
FIG. 2 is an explanatory drawing to illustrate how to obtain the G factor in the polarization characteristic measuring method and apparatus according to the present invention.

The polarization response correction described above is the one for the polarization characteristic measuring apparatus of dimension 0 (point); but the G factor cannot be obtained by the above method under such a microscope as the polarization characteristic measuring method and apparatus according to the present invention, because the direction of irradiation of the excitation light to the sample lies on the same line as the direction of observation of the fluorescence. Then, the polarization response correction is carried out as follows in this case. FIG. 2 is an explanatory drawing to illustrate how to obtain the G factor in the polarization characteristic measuring method and apparatus according to the present invention. The way for obtaining the G factor will be described for the case where the molecular axes of fluorescent probe molecules in the sample are distributed completely at random without being oriented and for the case where the molecular axes of fluorescent probe molecules in the sample are distributed in an oriented state.

First described is how to obtain the G factor in the case where the molecular axes of fluorescent probe molecules are distributed completely at random without being oriented in the sample.

Let $I_{pp}$, $I_{ps}$ be intensities (true values) of the respective p-polarized component and s-polarized component of fluorescence emitted under irradiation of the sample with the p-polarized excitation light with respect to a dichroic mirror being beam splitting means, and $I_{pp}'$, $I_{ps}'$ be actual values detected by the photodetector. Further, let $I_{sp}$, $I_{ss}$ be intensities (true values) of the respective p-polarized component and s-polarized component of fluorescence emitted under irradiation of the sample with the s-polarized excitation light with respect to the dichroic mirror, and $I_{sp}'$, $I_{ss}'$ be actual values detected by the photodetector. At this time there are the following relations among these values, the response $T_p$ of the receiving optical system and photodetector to the p-polarized light, and the response $T_s$ thereof to the s-polarized light.

$$I_{pp}' = T_p \cdot I_{pp}, \; I_{ps}' = T_s \cdot I_{ps} \tag{10}$$

$$I_{sp}' = T_p \cdot I_{sp}, \; I_{ss}' = T_s \cdot I_{ss} \tag{11}$$

The anisotropy ratio $P_2(p)$ obtained for irradiation with the p-polarized excitation light is expressed by the following equation.

$$P_2(p) = \frac{I_{pp} - I_{ps}}{I_{pp} + 2I_{ps}} = \frac{I_{pp}' - (T_p/T_s)I_{ps}'}{I_{pp}' + 2(T_p/T_s)I_{ps}'} \tag{12}$$

The anisotropy ratio $P_2(s)$ obtained for irradiation with the s-polarized excitation light is expressed by the following equation.

$$P_2(s) = \frac{I_{ss} - I_{sp}}{I_{ss} + 2I_{sp}} = \frac{I_{ss}' - (T_s/T_p)I_{sp}'}{I_{ss}' + 2(T_s/T_p)I_{sp}'} \tag{13}$$

Further, the G factor is expressed by the following equation.

$$G = \frac{T_p}{T_s} \tag{14}$$

Therefore, each of Eq. (12) and Eq. (13) is expressed as follows.

$$P_2(p) = \frac{I_{pp}' - G \cdot I_{ps}'}{I_{pp}' + 2G \cdot I_{ps}'} \tag{15}$$

$$P_2(s) = \frac{G \cdot I_{ss}' - I_{sp}'}{G \cdot I_{ss}' + 2I_{sp}'} \tag{16}$$

When the molecular axes of fluorescent probe molecules are distributed completely at random in the sample, the anisotropy ratio $P_2(p)$ obtained for irradiation with the p-polarized excitation light is equal to that $P_2(s)$ obtained for irradiation with the s-polarized excitation light as follows.

$$P_2(p) = P_2(s) \tag{17}$$

By substituting Eq. (15) and Eq. (16) into this Eq. (17), the G factor is given as follows.

$$G = [(I_{pp}' \cdot I_{sp}')/(I_{ps}' \cdot I_{ss}')]^{1/2} \tag{18}$$

Namely, in the case where the molecular axes of fluorescent probe molecules in the sample are distributed completely at random without being oriented, the G factor is obtained by measuring the intensities of the p-polarized component and the intensities of the s-polarized component of the fluorescence emitted under irradiation of the sample with the p-polarized excitation light and with the s-polarized excitation light and putting these intensities into Eq. (18). Then the polarization degree $P_1$ and anisotropy ratio $P_2$ can be obtained with high accuracy by effecting the polarization response correction with the G factor obtained in this way.

Next described is how to obtain the G factor in the case where the molecular axes of fluorescent probe molecules in the sample are distributed in the oriented state. Actually measured objects can be often approximated to this system.

If the way of obtaining the G factor in the case where the molecular axes of fluorescent probe molecules in the sample were distributed completely at random without being oriented, as described above, were applied to this case, the fluorescence would be measured as if the receiving optical elements except for the polarizing element, and the photodetector had anisotropy, though they had no anisotropy of polarization. Therefore, in the case where the molecular axes of fluorescent probe molecules in the sample are distributed in the oriented state, the assumption of Eq. (17) does not hold and the anisotropy ratio $P_2(p)$ obtained for irradiation with the p-polarized excitation light is normally different from that $P_2(s)$ obtained for irradiation with the s-polarized excitation light.

$$P_2(p) \neq P_2(s) \tag{19}$$

Namely, letting $I_{pp}$ and $I_{ps}$ be intensities of the respective p-polarized component and s-polarized component of the fluorescence emitted from the sample under irradiation with the p-polarized excitation light and $I_{sp}$ and $I_{ss}$ be intensities of the respective p-polarized component and s-polarized component of the fluorescence emitted from the sample under irradiation with the s-polarized excitation light, the following relation holds in the case where the molecular axes of fluorescent probe molecules in the sample are distributed completely at random:

$$\frac{I_{ps}}{I_{pp}} = \frac{I_{sp}}{I_{ss}}; \tag{20}$$

whereas the following relation holds in the case where the molecular axes of fluorescent probe molecules are distributed in the oriented state:

$$\frac{I_{ps}}{I_{pp}} \neq \frac{I_{sp}}{I_{ss}}. \tag{21}$$

Figure 3:
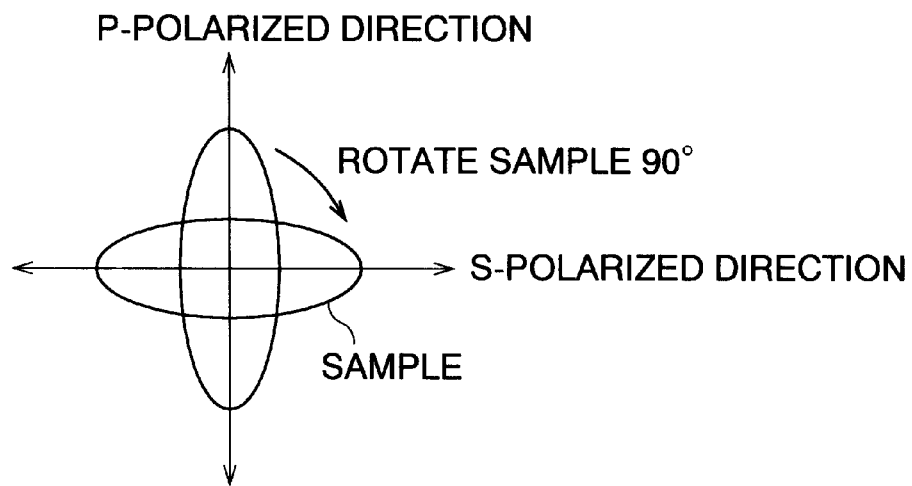
FIG. 3 is an explanatory drawing to illustrate how to obtain the G factor in the case where molecular axes of fluorescent probe molecules in a sample are distributed in an oriented state, in the polarization characteristic measuring method and apparatus according to the present invention.

Then, the G factor is obtained as follows in the case where the molecular axes of fluorescent probe molecules are distributed in the oriented state. Specifically, let $I_{pp}(0)$ and $I_{ps}(0)$ be intensities (true values) of the respective p-polarized component and s-polarized component of the fluorescence emitted from the sample under irradiation with the p-polarized excitation light and $I_{pp}(0)'$ and $I_{ps}(0)'$ be actual values detected by the photodetector. With the sample rotated by 90° about the center axis on the direction of irradiation of the excitation light as shown in FIG. 3, let $I_{sp}(90)$ and $I_{ss}(90)$ be intensities (true values) of the respective p-polarized component and s-polarized component of the fluorescence emitted from the sample under irradiation with the s-polarized excitation light and $I_{sp}(90)'$ and $I_{ss}(90)'$ be actual values detected by the photodetector. At this time there are the following relations among these values, the response $T_p$ of the receiving optical system and photodetector to the p-polarized light, and the response thereof $T_s$ to the s-polarized light.

$$I_{pp}(0)' = T_p \cdot I_{pp}(0), \; _{ps}(0)' = T_s \cdot I_{ps}(0) \tag{22}$$

$$I_{sp}(90)' = T_p \cdot I_{sp}(90), \; I_{ss}(90)' = T_s \cdot I_{ss}(90) \tag{23}$$

The anisotropy ratio $P_2(p,0)$ before the rotation of the sample is expressed by the following equation.

$$P_2(p, 0) = \frac{I_{pp}(0)' - (T_p/T_s)I_{ps}(0)'}{I_{pp}(0)' + 2(T_p/T_s)I_{ps}(0)'} \tag{24}$$

The anisotropy ratio $P_2(s,90)$ after the rotation of the sample by 90° is expressed by the following equation.

$$P_2(s, 90) = \frac{(T_p/T_s)I_{ss}(90)' - I_{sp}(90)'}{(T_p/T_s)I_{ss}(90)' + 2I_{sp}(90)'} \tag{25}$$

Here, each of Eq. (24) and Eq. (25) is expressed as follows, using the G factor represented by Eq. (14).

$$P_2(p, 0) = \frac{I_{pp}(0)' - G \cdot I_{ps}(0)'}{I_{pp}(0)' + 2G \cdot I_{ps}(0)'} \tag{26}$$

$$P_2(s, 90) = \frac{G \cdot I_{ss}(90)' - I_{sp}(90)'}{G \cdot I_{ss}(90)' + 2 \cdot I_{sp}(90)'} \tag{27}$$

When the molecular axes of fluorescent probe molecules in the sample are distributed in the oriented state, the anisotropy ratio $P_2(s,90)$ obtained for the irradiation with the s-polarized excitation light after the 90° rotation of the sample about the center axis on the irradiation direction of the excitation light is equal to that $P_2(p,0)$ obtained for the irradiation with the p-polarized excitation light before the rotation of the sample. Namely, the following relation holds.

$$P_2(s,90) = P_2(p,0) \tag{28}$$

Therefore, by substituting Eq. (26) and Eq. (27) into Eq. (28), the following equation is obtained.

$$\frac{G \cdot I_{ss}(90)' - I_{sp}(90)'}{G \cdot I_{ss}(90)' + 2 \cdot I_{sp}(90)'} = \frac{I_{pp}(0)' - G \cdot I_{ps}(0)'}{I_{pp}(0)' + 2G \cdot I_{ps}(0)'} \tag{29}$$

Solving this, the following is obtained as an equation representing the G factor.

$$G = [(I_{pp}(0)' \cdot I_{sp}(90)')/(I_{ps}(0)' \cdot I_{ss}(90)')]^{1/2} \tag{30}$$

Namely, the G factor in the case where the molecular axes of fluorescent probe molecules in the sample are distributed in the oriented state is obtained by making the 90° difference in the angle of rotation of the sample about the center axis on the irradiation direction of the excitation light between under the irradiation of the sample with the p-polarized excitation light and under the irradiation of the sample with the s-polarized excitation light, measuring the intensities of p-polarized component and the intensities of s-polarized component of the fluorescence generated under the irradiation of the sample with these excitation beams of the respective p-polarization and s-polarization, and putting these intensities into Eq. (30). Then the polarization degree $P_1$ and anisotropy ratio $P_2$ can be obtained with high accuracy by effecting the polarization response correction with the G factor obtained in this way.

In the polarization characteristic measuring method and apparatus according to the present invention, the polarization characteristics expressed by the following equations are further defined as quantities indicating polarization characteristics, different from the above-stated polarization degree $P_1$ and anisotropy ratio $P_2$.

$$P_3(p) = 1 - G \cdot \frac{I'_{ps}}{I'_{pp}} \tag{31}$$

$$P_4(p) = \frac{I'_{pp}}{I'_{ps}} - G \tag{32}$$

Figure 4:
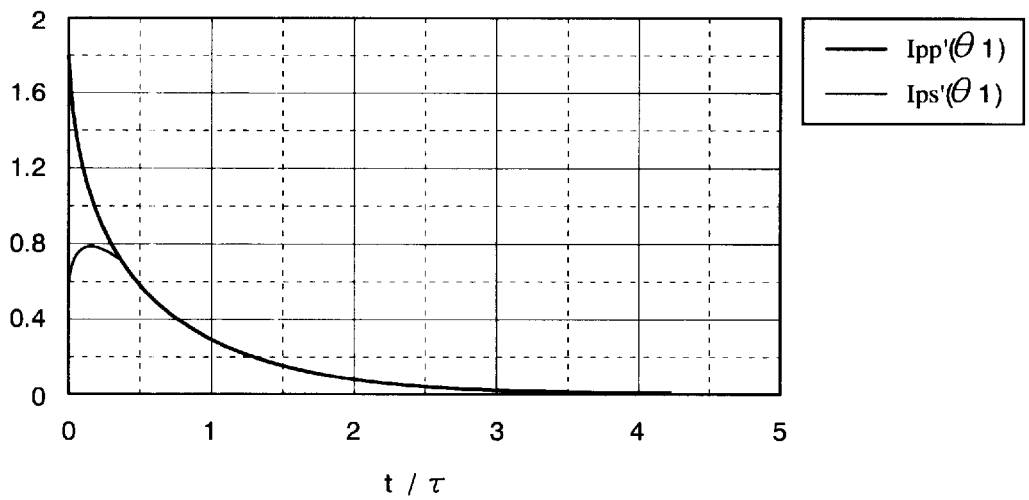
FIG. 4 is a graph to show decays of intensities of fluorescent polarized components parallel and perpendicular to the direction of the polarized excitation light, emitted from fluorescent molecules having the rotational correlation time of $\theta_1$.
Figure 5:
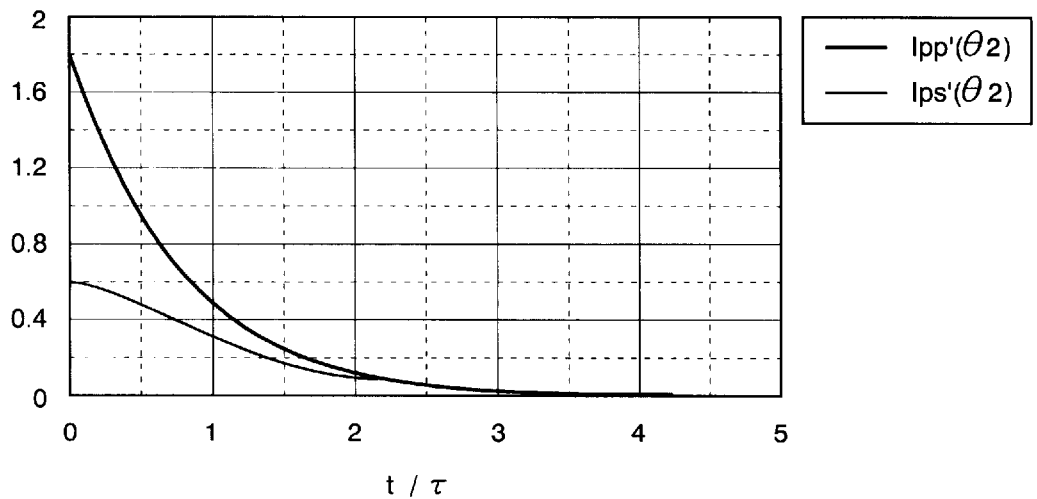
FIG. 5 is a graph to show decays of intensities of fluorescent polarized components parallel and perpendicular to the direction of the polarized excitation light, emitted from fluorescent molecules having the rotational correlation time of $\theta_2$.
Figure 6:
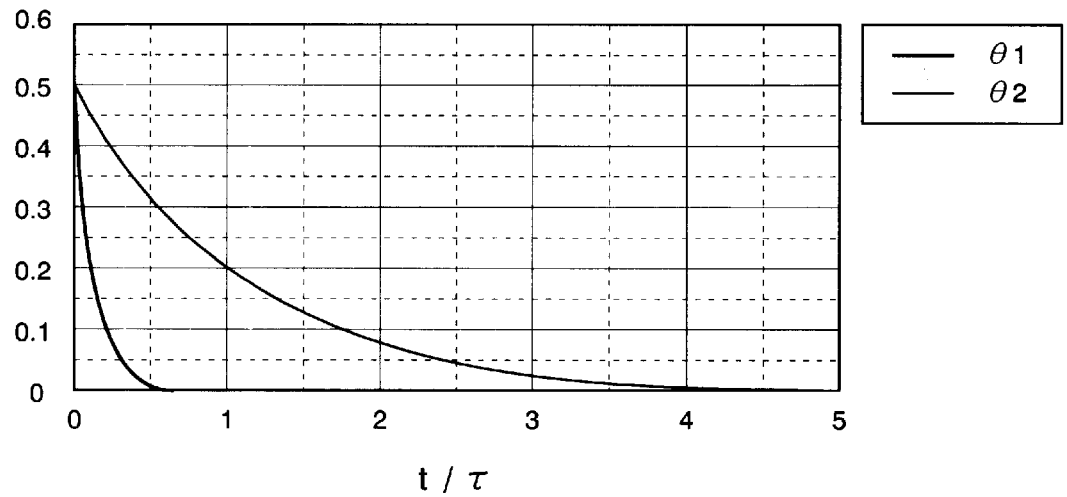
FIG. 6 is a graph to show decays of polarization characteristic $P_1$.
Figure 7:
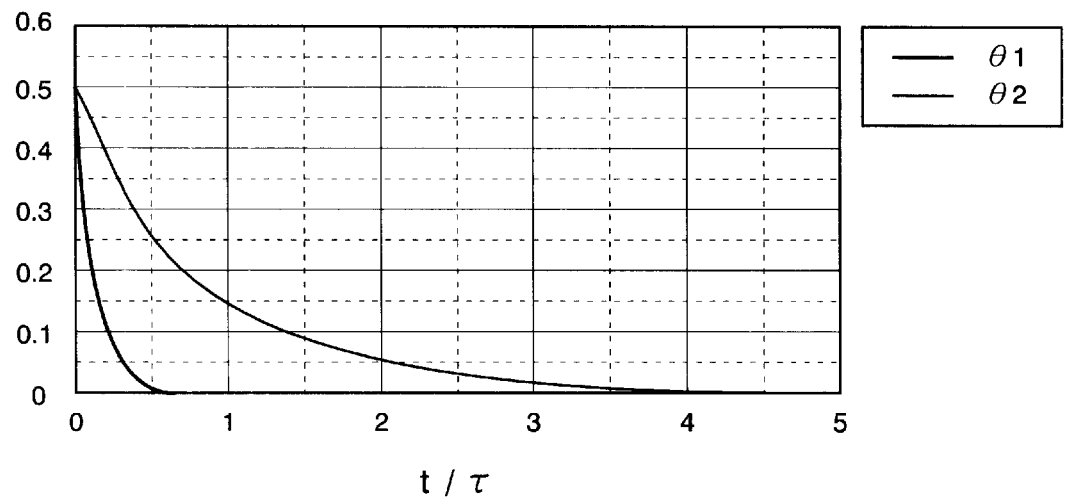
FIG. 7 is a graph to show decays of polarization characteristic $P_2$.
Figure 8:
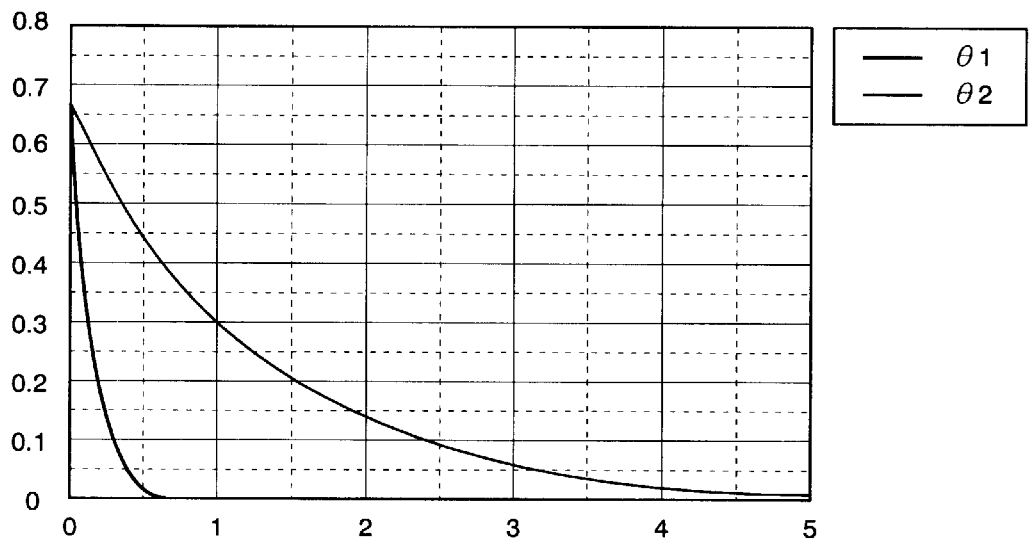
FIG. 8 is a graph to show decays of polarization characteristic $P_3$.
Figure 9:
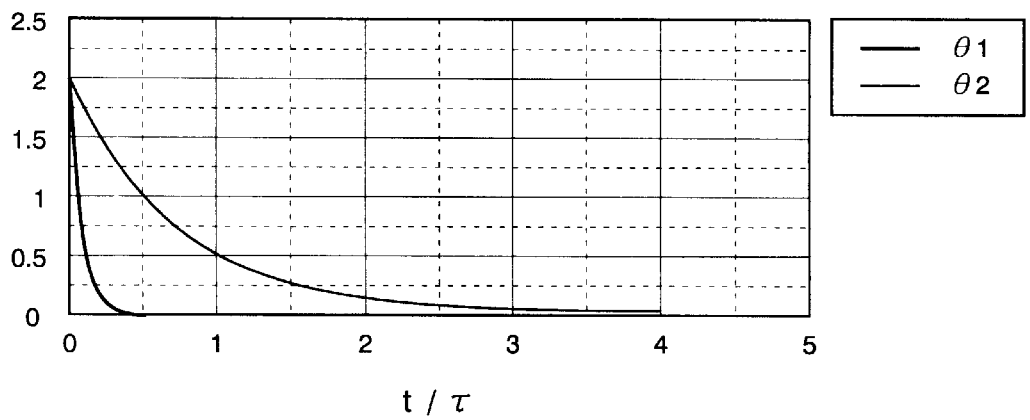
FIG. 9 is a graph to show decays of polarization characteristic $P_4$.

The polarization characteristics $P_3$ and $P_4$ are quantities that indicate relatively good agreement with the polarization degree $P_1$ and anisotropy ratio $P_2$. Let us now consider two types of fluorescent molecules having the same fluorescence lifetime $\tau$ and different rotational correlation times $\theta$ (quantities featuring the speed of rotational Brownian motion). FIG. 4 and FIG. 5 show results of simulations about the intensity of fluorescence polarized components $I_{pp}'$ and $I_{ps}'$, parallel and perpendicular to the polarized direction of the excitation light when each of fluorescence from the two types of fluorescent molecules was measured separately by the system of G=1 under excitation with pulsed light. The calculation was conducted under the assumption that $\theta_1$ was 0.1 times $\tau$ and $\theta_2$ was 10 times $\theta_1$. FIG. 6 to FIG. 9 show results of calculation of the polarization characteristics $P_1$ by Eq. (4), $P_2$ by Eq. (5), $P_3$ by Eq. (31), and $P_4$ by Eq. (32), based on the above data. As seen from the drawings, the polarization characteristics $P_1$, $P_2$, $P_3$, and $P_4$ provide decay patterns that nearly agree with each other against changes in time and $\theta$.

As apparent from comparison of Eq. (31) and Eq. (32) with Eq. (4) and Eq. (5) which are the equations for respectively defining the polarization degree $P_1$ and anisotropy ratio $P_2$, the polarization characteristics $P_3$ and $P_4$ can be calculated by less computational complexity than that for the computation to obtain the polarization degree $P_1$ and anisotropy ratio $P_2$. Hence, the computation of the polarization characteristics $P_3$ and $P_4$ by the arithmetics using Eq. (31) and Eq. (32) is extremely effective for obtaining the polarization characteristics within a short time, for example, for measuring changes of the polarization characteristics in real time and for obtaining the polarization characteristics for two-dimensional large data. The decrease of computational complexity also decreases errors on the occasion of computation.

Figure 10:
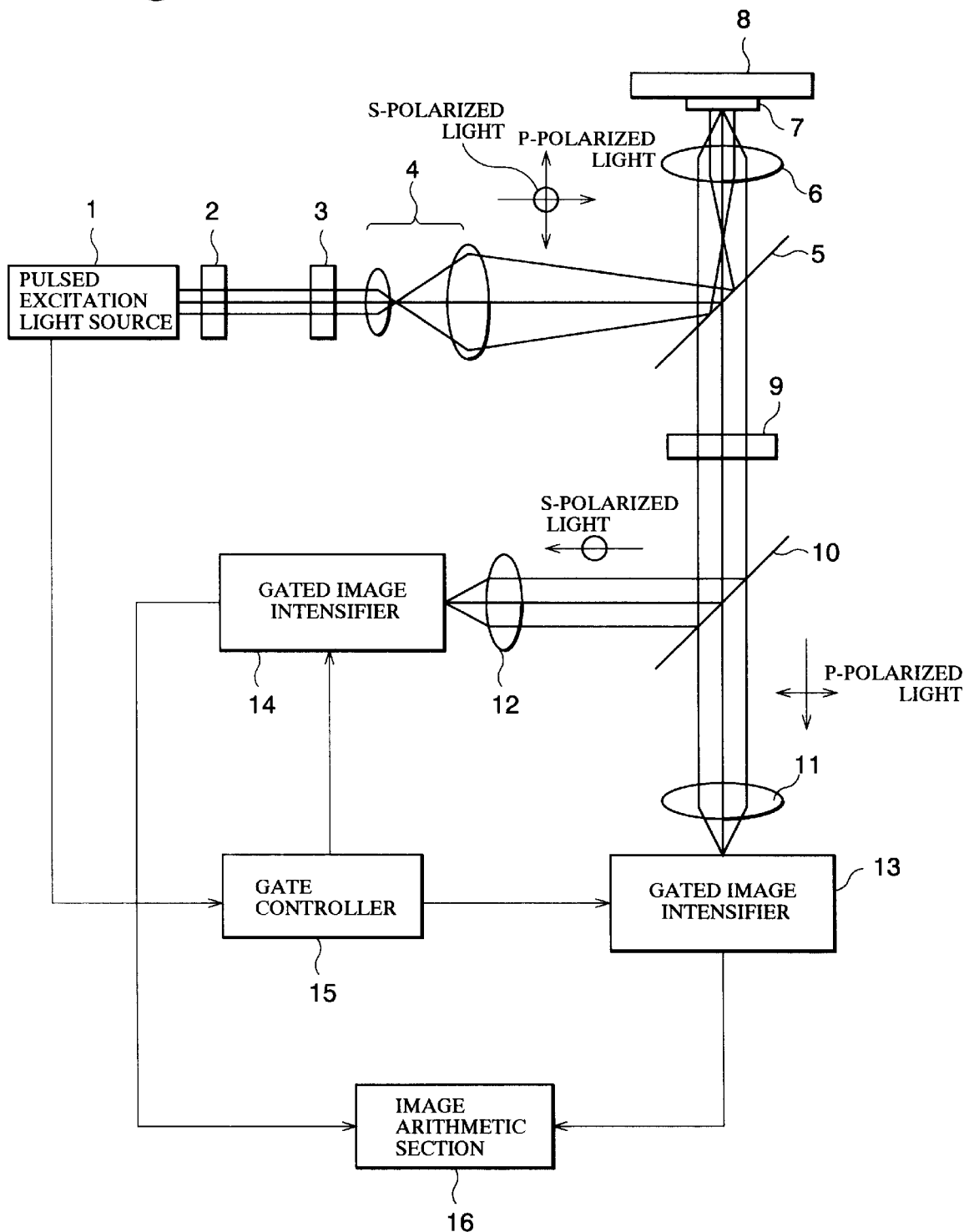
FIG. 10 is a structural drawing of the polarization characteristic measuring apparatus according to the present invention.

Next described is the structure of the polarization characteristic measuring apparatus according to the present invention. FIG. 10 is a drawing to show the structure of the polarization characteristic measuring apparatus according to the present invention.

Pulsed excitation light source 1 is a light source for radiating the pulsed excitation light (the first beam) for exciting the fluorescent probe in the sample 7. The pulsed excitation light radiated from the pulsed excitation light source 1 is converted into linearly polarized light by polarizer 2 and thereafter the light is incident into a half-wave plate (polarized direction rotating means) 3 to be rotated into either of the p-polarized direction and the s-polarized direction with respect to dichroic mirror (beam splitting means) 5. The pulsed excitation light becoming either p-polarized light or s-polarized light is guided through objective lens 6 to irradiate the sample 7. More specifically, the pulsed excitation light is shaped into predetermined beam diameter and configuration by excitation light introducing optical system 4 and the beam is reflected by the dichroic mirror 5 and converged by the objective lens 6 to irradiate the observation area on the sample 7 placed on a sample stage (sample rotating means) 8. This sample stage 8 is one capable of rotating the sample 7 about the optical axis of the pulsed excitation light incident into the sample 7.

When the sample 7 is exposed to the pulse excitation light, the fluorescent probe in the sample 7 emits fluorescence (the second beam). An intensity distribution of the fluorescence is measured by detecting means while separating a beam emitted in the same direction as the irradiation direction of excitation light, into p-polarized light and s-polarized light. More specifically, the beam incident into the objective lens 6 among the fluorescence emitted from the sample 7 travels through the objective lens 6, further through dichroic mirror 5 and through band-pass filter 9, then it is split into the p-polarized component and s-polarized component by polarizing beam splitter 10, and fluorescence polarized images of the respective p-polarized component and s-polarized component are formed on image photocathode of respective gated image intensifiers 13 and 14 by imaging lenses 11 and 12, respectively. Then intensity distributions are measured by the respective gated image intensifiers 13 and 14.

Here, the band-pass filter 9 transmits the fluorescence but absorbs scattered light of the pulse excitation light generated in the sample 7, and the polarizing beam splitter 10 transmits the p-polarized component of the fluorescence but reflects the s-polarized component thereof. Each of the gated image intensifiers 13 and 14 opens or closes the gate, based on a gate signal outputted from gate controller 15, and picks up a fluorescence polarization image formed on the photocathode during the opening period of the gate. The gate controller 15 outputs the gate signal that indicates opening of each gate of the gated image intensifiers 13 and 14 only during a period $\Delta t$ from time $t_0$, while defining the reference time at the timing when the pulsed excitation light is radiated from the pulsed excitation light source 1.

The fluorescence polarized images of the respective p-polarized component and s-polarized component picked up by the respective gated image intensifiers 13 and 14 are supplied to image arithmetic section 16. The image arithmetic section 16 performs the polarization response correction, based on these fluorescence polarized images, thereby obtaining two-dimensional images of the polarization characteristics ($P_1$, $P_2$, $P_3$, $P_4$).

Next described is a method for gaining a two-dimensional image of the anisotropy ratio $P_2$ of the fluorescence with the polarization response correction by use of this polarization characteristic measuring apparatus. Two-dimensional images of the respective polarization characteristics $P_1$, $P_3$, and $P_4$ are also obtained in the same manner. This polarization response correction and the two-dimensional image of the anisotropy ratio $P_2$ of fluorescence are achieved by arithmetic in the image arithmetic section 16. Discussed in the following description are two different cases where the molecular axes of fluorescent probe molecules in the sample 7 are distributed completely at random without being oriented and where the molecular axes of fluorescent probe molecules in the sample 7 are distributed in the oriented state.

In the case where the molecular axes of fluorescent probe molecules in the sample 7 are distributed completely at random without being oriented, the two-dimensional image of the anisotropy ratio $P_2$ is acquired as follows.

In this case, by properly setting the optic axis of the half-wave plate 3, the pulsed excitation light outputted from the pulsed excitation light source 1 is converted into the p-polarized light to irradiate the sample 7. At this time, let $I_{pp}(t_0,\Delta t)$ and $I_{ps}(t_0,\Delta t)$ be fluorescence images of the respective p-polarized light and s-polarized light picked up by the respective gated image intensifiers 13 and 14 during the period $\Delta t$ from the time $t_0$ according to instructions of the gate signal from the gate controller 15.

Similarly, by properly setting the optic axis of the half-wave plate 3, the pulsed excitation light outputted from the pulsed excitation light source 1 is converted into the s-polarized light to irradiate the sample 7. At this time, let $I_{sp}(t_0,\Delta t)$ and $I_{ss}(t_0,\Delta t)$ be fluorescence images of the respective p-polarized light and s-polarized light picked up by the respective gated image intensifiers 13 and 14 according to instructions of the gate signal from the gate controller 15.

Then the G factor concerning the polarization response correction is obtained by the following equation.

$$G = [(I_{pp}(t_0,\Delta t) \cdot I_{sp}(t_0,\Delta t))/(I_{ps}(t0,\Delta t) \cdot Iss(t0,\Delta t))]^{1/2} \qquad (33)$$

The anisotropy ratio $P_2(p,t_0,\Delta t)$ is obtained according to the following equation.

$$P_2(p, t_0, \Delta t) = \frac{I_{pp}(t_0, \Delta t) - G \cdot I_{ps}(t_0, \Delta t)}{I_{pp}(t_0, \Delta t) + 2G \cdot I_{ps}(t_0, \Delta t)} \qquad (34)$$

The fluorescence images $I_{pp}(t_0,\Delta t)$, $I_{ps}(t_0,\Delta t)$, $I_{sp}(t_0,\Delta t)$, and $I_{ss}(t_0,\Delta t)$, the G factor, and the anisotropy ratio $P_2(p,t_0,\Delta t)$ all are functions of coordinates (x, y) on the plane perpendicular to the optical axis of the pulsed excitation light irradiating the sample 7. The two-dimensional image of the anisotropy ratio $P_2$ of the fluorescence emitted from the fluorescent probe in the sample can be measured with high accuracy in this way.

In the case where the molecular axes of fluorescent probe molecules in the sample 7 are distributed in the oriented state, the two-dimensional image of the anisotropy ratio $P_2$ is acquired as follows.

In this case, by properly setting the optic axis of the half-wave plate 3, the pulsed excitation light outputted from the pulsed excitation light source 1 is converted into the p-polarized light to irradiate the sample 7. At this time, $I_{pp}(0,t_0,\Delta t)$ and $I_{ps}(0,t_0,\Delta t)$ be fluorescence images of the respective p-polarized light and s-polarized light picked up by the respective gated image intensifiers 13 and 14 during the period $\Delta t$ from the time $t_0$ according to instructions of the gate signal from the gate controller 15.

Subsequently, the sample 7 is rotated 90° by rotation of the sample stage 8 and thereafter, similarly by properly setting the optic axis of the half-wave plate 3, the pulsed excitation light outputted from the pulsed excitation light source 1 is converted into the s-polarized light to irradiate the sample 7. At this time, let $I_{sp}(90,t_0,\Delta t)$ and $I_{ss}(90,t_0,\Delta t)$ be fluorescence images of the respective p-polarized light and s-polarized light picked up by the respective gated image intensifiers 13 and 14 according to instructions of the gate signal from the gate controller 15.

Then the G factor concerning the polarization response correction is obtained by the following equation.

$$G=[(I_{pp}(0,t_0,\Delta t)\cdot I_{sp}(90,t_0,\Delta t))/(I_{ps}(0,t_0,\Delta t)\cdot s_{ss}(90,t_0,\Delta t))]^{1/2} \quad (35)$$

The anisotropy ratio $P_2(p,t_0,\Delta t)$ of the fluorescence during irradiation of the sample with the p-polarized excitation light is obtained by the following equation.

$$P_2(p, t_0, \Delta t) = \frac{I_{pp}(0, t_0, \Delta t) - G \cdot I_{ps}(0, t_0, \Delta t)}{I_{pp}(0, t_0, \Delta t) + 2G \cdot I_{ps}(t_0, \Delta t)} \quad (36)$$

The fluorescence images $I_{pp}(0,t_0,\Delta t)$, $I_{ps}(0,t_0,\Delta t)$, $I_{sp}(90, t_0,\Delta t)$, and $I_{ss}(90,t_0,\Delta t)$, the G factor, and the anisotropy ratio $P_2(p,t_0,\Delta t)$ all are functions of coordinates (x, y) on the plane perpendicular to the optical axis of the pulsed excitation light irradiating the sample 7. The two-dimensional image of the anisotropy ratio $P_2$ of the fluorescence emitted from the fluorescent probe bound to the target can be measured with high accuracy in this way.

Next described are results of experiments conducted about the polarization response correction in the polarization characteristic measuring apparatus according to the present invention. Specific components of the polarization characteristic measuring apparatus used herein are as follows. The pulsed excitation light source 1 was a mode-locked Ti:sapphire laser light source, and the pulsed excitation light irradiating the sample 7 was the second harmonic radiated from the light source (the wavelength 400 nm, the pulsewidth 200 fsec, the repetition rate 100 kHz). The polarizer 2 was a Glan-laser prism and the half-wave plate 3 was a Fresnel rhomb half wave plate. The gated image intensifiers 13 and 14 were replaced each by microchannel plate photomultiplier tubes herein and the fluorescence intensities were measured by the time-correlated single-photon counting method (TCSPC method). The sample 7 was 17 mer oligonucleotide labeled with FITC (Fluorescein isothiocyanato). In this sample the molecular axes of fluorescent probe molecules are distributed completely at random without being oriented. Accordingly, the G factor was obtained by Eq. (18) and the anisotropy ratio $P_2$ of fluorescence by Eq. (15).

Figure 11:
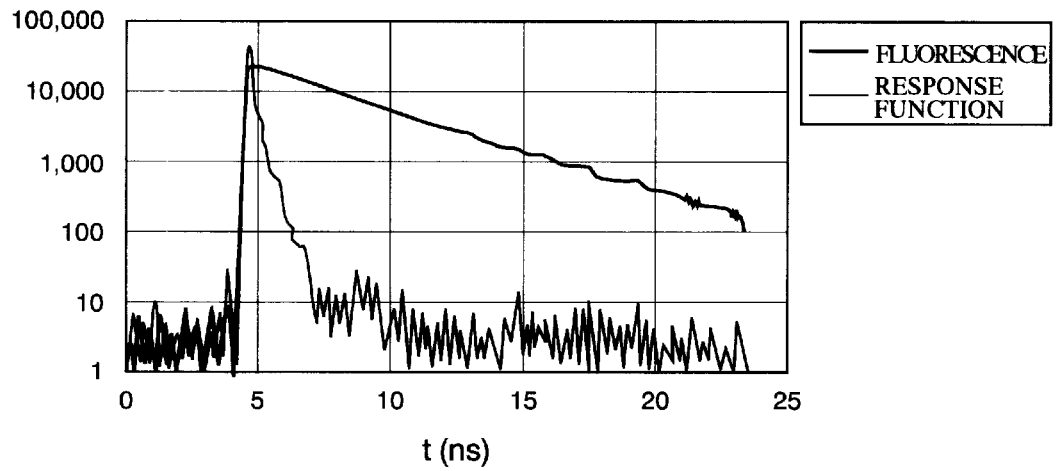
FIG. 11 is a graph to show a decay (thick line) obtained when intensities of fluorescence emitted from the sample are measured without intervention of a polarizing device, and a response function (thin line) of the apparatus under the microscope.
Figure 12:
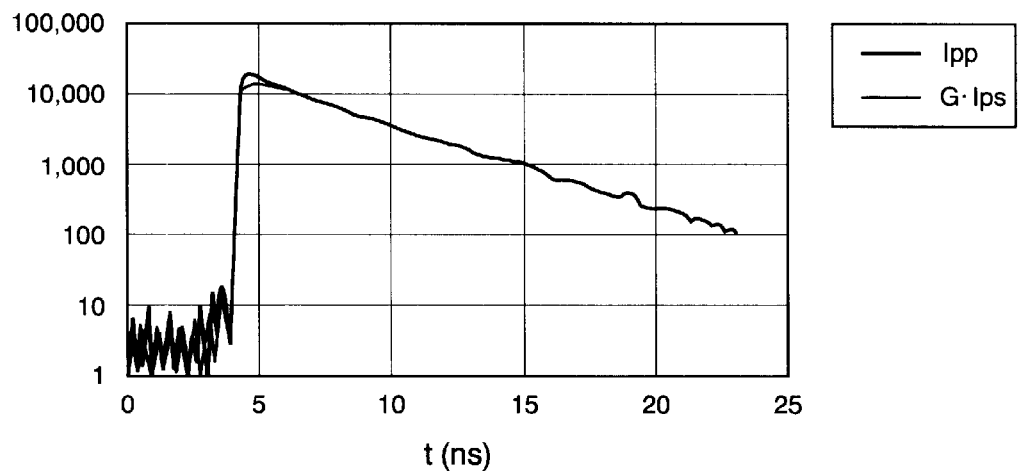
FIG. 12 is a graph to show decays of respective p-polarized component (thick line) and s-polarized component (thin line) of fluorescence emitted when the sample is excited with pulsed excitation light of p-polarization.

FIG. 11 is a graph to show a decay (thick line) of intensity of fluorescence from the sample, which was measured without intervention of the polarizing device, and a response function (thin line) of the apparatus under the microscope. FIG. 12 is a graph to show decays of the respective p-polarized component (thick line) and s-polarized component (thin line) of the fluorescence emitted from the sample 7 when it was excited with the pulsed excitation light of p-polarization. In this FIG. 12 the decay of the s-polarized component (thin line) is illustrated by values obtained by multiplying actual values by the G factor.

Figure 13:
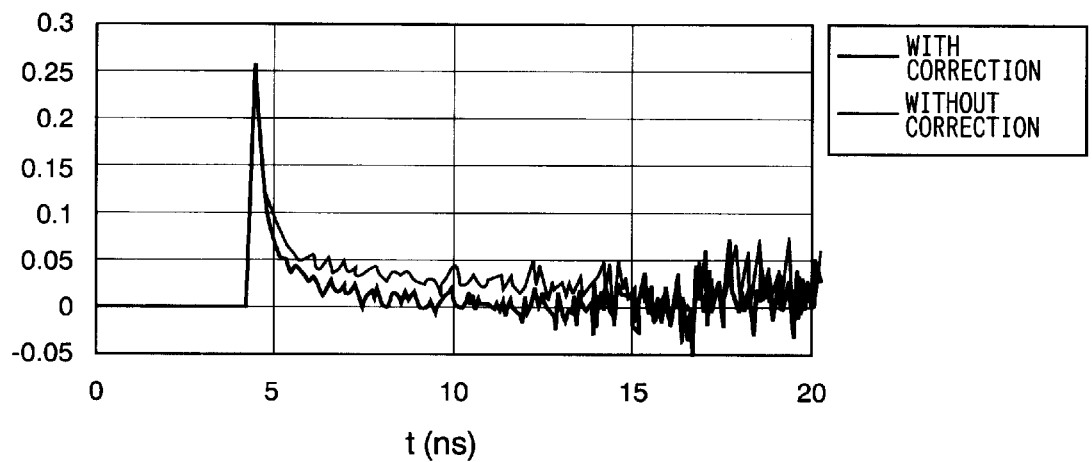
FIG. 13 is a graph to show a decay (thick line) of anisotropy ratio $P_2$ obtained with execution of the polarization response correction by the G factor, and a decay (thin line) of anisotropy ratio $P_2$ obtained without execution of the polarization response correction.

FIG. 13 is a graph to show a decay (thick line) of the anisotropy ratio $P_2$ obtained with execution of the polarization response correction by the G factor and a decay (thin line) of the anisotropy ratio $P_2$ obtained without execution of the polarization response correction. Namely, the thick line is the decay of the anisotropy ratio $P_2$ obtained in such a way that the G factor was gained based on the results of polarization measurement of fluorescence emitted from the sample 7 when it was excited with the pulsed excitation light of p-polarization and with the pulsed excitation light of s-polarization and that the polarization response correction by the G factor was effected on the measured values of intensities of the respective p-polarized component and s-polarized component of the fluorescence emitted from the sample 7 when it was excited with the pulsed excitation light of p-polarization. On the other hand, the thin line indicates the decay of the anisotropy ratio $P_2$ obtained without effecting the polarization response correction by the G factor, under the assumption that the measured values are true values. The value of the G factor was 1.076. In this apparatus the dichroic mirror 5 is considered to mainly contribute to the G factor.

Figure 14:
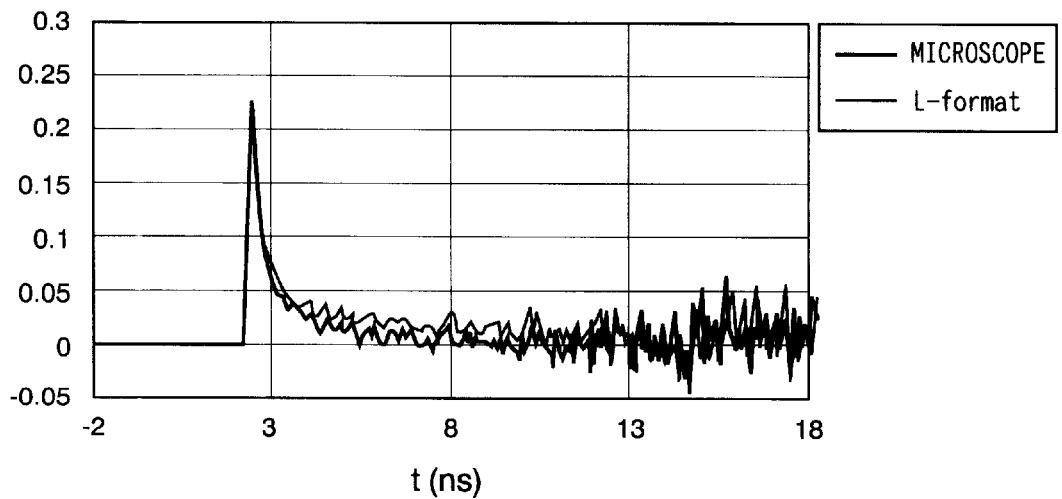
FIG. 14 is a graph to show a decay (thick line) of anisotropy ratio $P_2$ obtained with execution of the polarization response correction in the polarization characteristic measuring apparatus according to the present invention, and a decay (thin line) of anisotropy ratio $P_2$ obtained with execution of the polarization response correction in the polarization characteristic measuring apparatus of the conventional structure.

FIG. 14 is a graph to show a decay (thick line) of the anisotropy ratio $P_2$ obtained with execution of the polarization response correction under such a microscope as the polarization characteristic measuring apparatus according to the present invention (the configuration of FIG. 2) and a decay (thin line) of the anisotropy ratio $P_2$ obtained with execution of the polarization response correction in the polarization characteristic measuring apparatus of the conventional structure (the configuration of FIG. 1). As illustrated in this figure, they show good agreement. Namely, it was verified that the accurate anisotropy ratio $P_2$ was also able to be measured by effecting the polarization response correction under such a microscope as the polarization characteristic measuring apparatus according to the present invention.

Next described are measurement results of fluorescence polarization characteristic using the polarization characteristic measuring apparatus according to the present invention. Specific components of the polarization characteristic measuring apparatus used herein are as follows. The pulsed excitation light source 1 was a mode-locked Ti:sapphire laser light source, and the pulsed excitation light irradiating the sample 7 was the second harmonic radiated from the light source (the wavelength 465 nm, the pulsewidth 200 fsec, the repetition rate 100 kHz). The polarizer 2 was a Glan-laser prism and the half wave plate 3 was a Fresnel rhomb half-wave plate. For measuring the decays of fluorescence, the gated image intensifiers 13 and 14 were replaced each by microchannel plate photomultiplier tubes herein and the fluorescence intensities were measured by the time-correlated single photon counting method (TCSPC method).

The sample 7 was NG cell (NG108-15) and the fluorescent probe was HDAF (5-(N-hexadecanoyl) aminofluorescein), which was able to be bound in a specific manner to a cell membrane. The concentration of the dye was 10 $\mu$M and the time for staining was 30 minutes. In this sample 7 the molecular axes of fluorescent probe molecules are distributed completely at random without being oriented on the plane perpendicular to the optical axis of received light. Accordingly, the G factor was gained by Eq. (18) and the anisotropy ratio $P_2$ by Eq. (15).

Figure 15:
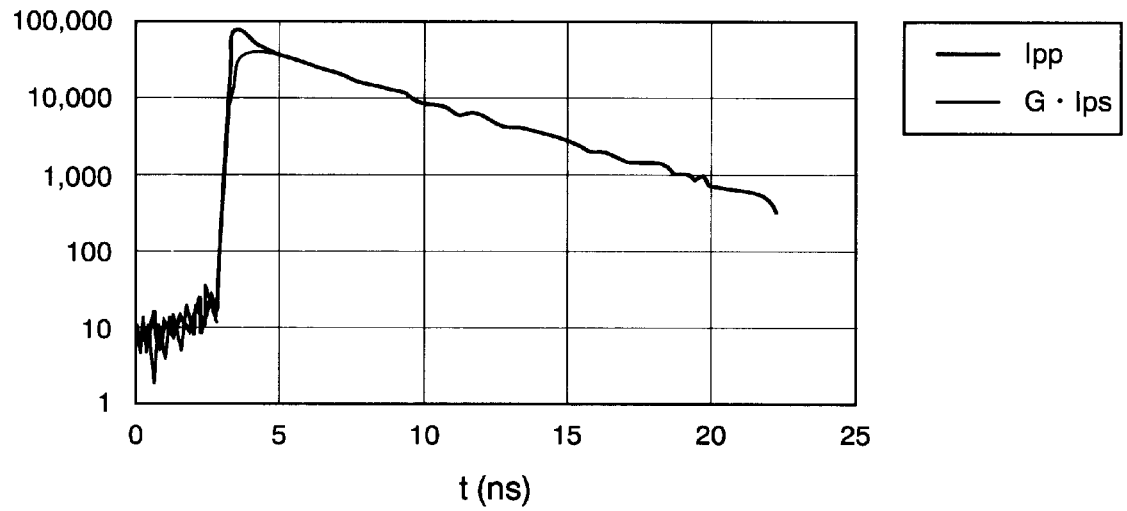
FIG. 15 is a graph to show decays of the respective p-polarized component (thick line) and s-polarized component (thin line) of fluorescence emitted when HDAF solution is excited with the pulsed excitation light of p-polarization.
Figure 16:
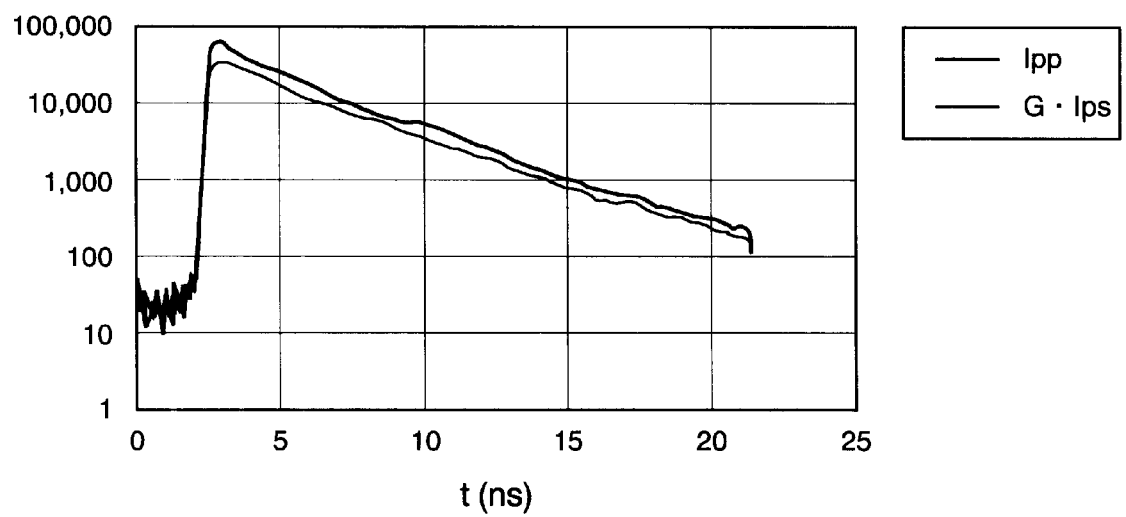
FIG. 16 is a graph to show decays of the respective p-polarized component (thick line) and s-polarized component (thin line) of fluorescence emitted when an HDAF-stained NG cell is excited with by the pulsed excitation light of p-polarization.

FIG. 15 is a graph to show decays of the respective p-polarized component (thick line) and s-polarized component (thin line) of fluorescence emitted when the free fluorescent probe (HDAF solution) was excited with the pulsed excitation light of p-polarization. In this figure the decay of the s-polarized component (the thin line) is indicated by values obtained by multiplying actual values by the G factor. FIG. 16 is a graph to show decays of the respective p-polarized component (thick line) and s-polarized component (thin line) of fluorescence emitted when the fluorescent probe bound to the target (HDAF-stained NG cell) was excited with the pulsed excitation light of p-polarization. In this figure the decay of the s-polarized component (the thin line) is also indicated by values obtained by multiplying actual values by the G factor.

Figure 17:
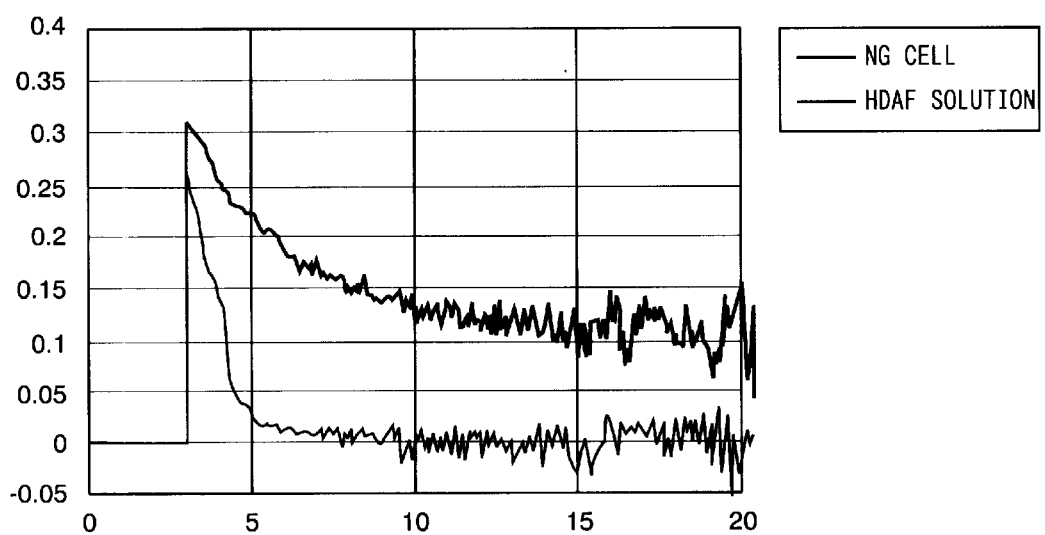
FIG. 17 is a graph to show decays of anisotropy ratio $P_2$ obtained with execution of the polarization response correction by the G factor for the fluorescence emitted when the HDAF solution (thin line) and HDAF-stained NG cell (thick line) are excited.

FIG. 17 is a graph to show decays of the anisotropy ratio $P_2$ obtained with execution of the polarization response correction by the G factor for the fluorescence emitted when the HDAF solution (thin line) and the HDAF-stained NG cell (thick line) were excited. Namely, the thin line is a decay of the anisotropy ratio $P_2$ where the fluorescent probe is free and the thick line is a decay of the anisotropy ratio $P_2$ where the fluorescent probe is bound to the target. As seen from the figure, the free fluorescent probe demonstrates quicker lowering of polarization characteristic (or is depolarized more quickly) than the fluorescent probe bound to the target. Therefore, the fluorescent probe bound to the target and the free fluorescent probe can be distinguished from each other by measuring degrees of depolarization.

Figure 18:
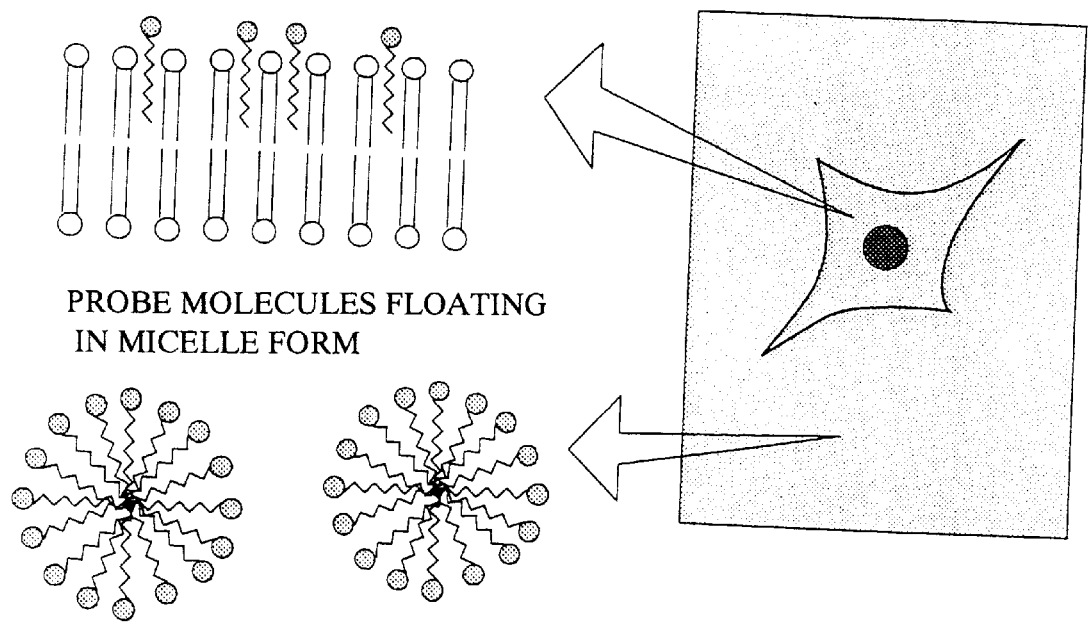
FIG. 18 is a schematic diagram of a sample in which free molecules of the fluorescent probe (HDAF solution) and molecules of the fluorescent probe bound to the target (HDAF-stained NG cell) coexist.

Then the polarization characteristic of the fluorescence was two-dimensionally analyzed in a sample in which the free fluorescent probe (HDAF solution) and the fluorescent probe bound to the target (HDAF-dyed NG cell) coexist as shown in the schematic diagram of FIG. 18. First, when the fluorescence from the sample was measured without intervention of the polarizing device, the two-dimensional distribution of fluorescence intensity (normal fluorescence image) had the mean I(F)=36655 (standard deviation τ(F)=1863) in the region where the fluorescent probe was present in the free state (in the free region) and the mean I(B)=43864 (standard deviation σ(B)=3378) in the region where the fluorescent probe was bound to the target (in the bound region). When the contrast C(I) was calculated by the following equation from these values, it was very low, 0.09.

$$C(I) = \frac{I(B) - I(F)}{I(B) + I(F)} \tag{37}$$

In addition thereto, there was also two-dimensional unevenness of intensity of the excitation light, so that the difference between the free region and the bound region was not clear. Next, a two-dimensional image of the anisotropy ratio $P_2$ of the fluorescence from the sample was measured with the gates of the gated image intensifiers 13 and 14 being always kept open (DC measurement). As a result, the mean value of the anisotropy ratio $P_2$ was $P_2(F)=0.044$ in the free region and the mean $P_2(B)=0.086$ in the bound region as shown in FIG. 19. The contrast $C(P_2)$ was computed by the following equation from these values.

$$C(P_2) = \frac{P_2(B) - P_2(F)}{P_2(B) + P_2(F)} \tag{38}$$

The contrast was 0.32 and it became possible to definitely distinguish the free region from the bound region. Further, the anisotropy ratio $P_2$ of the fluorescence from the sample was measured while opening the gates of the gated image intensifiers 13 and 14 during only the period 3 ns from the time $t_0=2$ ns (which was set at the time when the free fluorescent probe was sufficiently depolarized, while defining 0 ns at the time when it was excited by the pulsed light) (time-resolved measurement). As a result, the mean value of the anisotropy ratio $P_2$ was $P_2=0.016$ in the free region and the mean $P_2=0.069$ in the bound region as shown in FIG. 19. When the contrast was calculated by Eq. (38) from these values, it was 0.62. Namely, in the two-dimensional image of the anisotropy ratio $P_2$, the contrast between the free region and the bound region was improved by the time-resolved measurement as compared with the DC measurement. It is seen from the above result that the position where the fluorescent probe bound to the target exists can be specified by measuring the two-dimensional image of polarization characteristic of fluorescence under the microscope.

Next described is a method for physically (optically) canceling the polarization characteristics of the dichroic mirror 5, which are considered to mainly contribute to the polarization response correction factor in the polarization characteristic measuring apparatus according to the present invention.

FIG. 20A and FIG. 20B are drawings to show the structure of a detection optical system in the polarization characteristic measuring apparatus for canceling the polarization characteristics of the dichroic mirror 5, which are views observed along two mutually orthogonal directions perpendicular to the optical axis of the detection optical system. The detection optical system shown in FIG. 20A and FIG. 20B corresponds to that from the sample stage 8 to the polarizing beam splitter 10 in the polarization characteristic measuring apparatus shown in FIG. 10 and the same elements are denoted by the same reference symbols. The structure of the other parts than this detection optical system is the same as that of the corresponding parts in the polarization characteristic measuring apparatus shown in FIG. 10.

The detection optical system shown in FIG. 20A and FIG. 20B is obtained by interposing a second dichroic mirror 17 on the optical path between the first dichroic mirror 5 and the band-pass filter 9 in the detection optical system of the polarization characteristic measuring apparatus shown in FIG. 10. This second dichroic mirror 17 is the one having the same characteristics as the first dichroic mirror 5 and set in the orientation achieved by rotating the first dichroic mirror 5 90° about the optical axis.

With this detection optical system, the linearly-polarized excitation light of p-polarization or s-polarization with respect to the dichroic mirror 5 is incident to the first dichroic mirror 5 to be reflected thereby and then be guided through the objective lens 6 to irradiate the sample 7 on the sample stage 8. The fluorescence generated in the sample 7 under irradiation with the excitation light travels through the objective lens 6 and then through the dichroic mirrors 5 and 17 successively to reach the band-pass filter 9. Since the dichroic mirrors 5 and 17 have the same characteristics, their responses $T_p$ to the p-polarized light are equal to each other in the dichroic mirrors 5 and 17 and their responses $T_s$ to the s-polarized light are also equal in the dichroic mirrors 5 and 17.

Accordingly, letting $I_p(0)$ be the intensity of the p-polarized component (with respect to the dichroic mirror 5) of the fluorescence having been generated in the sample 7 and having passed through the objective lens 6, the intensity $I_p(1)$ of this polarization component after passage through the first dichroic mirror 5 is given by the following equation.

$$I_p(1)=T_p \cdot I_p(0) \tag{39}$$

Further, the intensity $I_p(2)$ of the p-polarized component of the fluorescence after passage through the second dichroic mirror 17 is given as follows.

$$I_p(2)=T_s \cdot I_p(1)=T_s \cdot T_p \cdot I_p(0) \tag{40}$$

On the other hand, letting $I_s(0)$ be the intensity of the s-polarized component (with respect to the dichroic mirror 5) of the fluorescence having been generated in the sample 7 and having passed through the objective lens 6, the intensity $I_s(1)$ of this polarization component after passage through the first dichroic mirror 5 is given by the following equation.

$$I_s(1)=T_s \cdot I_s(0) \tag{41}$$

Further, the intensity $I_s(2)$ of the s-polarized component of the fluorescence after passage through the second dichroic mirror 17 is given as follows.

$$I_s(2)=T_p \cdot I_s(1)=T_p \cdot T_s \cdot I_s(0) \qquad (42)$$

Namely, the following relation holds.

$$\frac{I_p(2)}{I_p(0)} = \frac{I_s(2)}{I_s(0)} = T_p \cdot T_s \qquad (43)$$

Thus, the responses of the dichroic mirrors 5 and 17 are equal to each other to either of the p-polarized component and s-polarized component of fluorescence.

In the receiving optical system (the optical system from the sample to the photodetector) of the polarization characteristic measuring apparatus shown in FIG. 10, the difference between the responses to the fluorescence of p-polarization and s-polarization (with respect to the dichroic mirror 5) is caused mainly by the dichroic mirror 5. In contrast, in the case of the receiving optical system of the polarization characteristic measuring apparatus having the detection optical system shown in FIG. 20A and FIG. 20B, the responses to the fluorescence of p-polarization and s-polarization (with respect to the dichroic mirror 5) are equal in the dichroic mirrors 5 and 17, so that the difference is small between the responses to the fluorescence of p-polarization and s-polarization in the entire receiving optical system.

Since the polarization characteristic measuring apparatus having the detection optical system shown in FIG. 20A and FIG. 20B includes the second dichroic mirror 17 in addition to the first dichroic mirror 5, the polarization response characteristics of the receiving optical system are improved; and the polarization characteristic of fluorescence can be measured with high accuracy by effecting the polarization response correction based on the G factor.

The polarization characteristic measuring method and apparatus described above can be applied to the both cases of one-photon excitation and multiple photon excitation. However, the effect is more prominent in the case of multiple photon excitation than in the case of one-photon excitation. The case of two-photon excitation will thus be explained below in comparison with the case of one-photon excitation.

Measurement of polarization characteristic is measurement which is carried out in such a way that the sample is exposed to the linearly polarized excitation light to selectively excite molecules having the molecular axis along a specific direction out of those of the fluorescent probe in the sample and that the polarization characteristic of fluorescence generated thereby is measured and by which the speed or the like of the rotational Brownian motion of the fluorescent probe is detected based on the polarization characteristic measured. It is, therefore, desirable to excite only the fluorescent probe molecules having the molecular axis along the direction parallel to the polarized direction of the excitation light. In practice, however, molecules of the fluorescent probe having molecular axes along directions different from the polarized direction of the excitation light are also excited in a certain probability.

Let us define a as an angle between the polarized direction of the excitation light and the direction of the molecular axis of the fluorescent probe. Then the amplitude of the excitation light in the direction of the molecular axis of the fluorescent probe is proportional to cos α. In the case of one-photon excitation, the probability (excitation probability) $P_{1p}$ in which a fluorescent probe is excited is proportional to the intensity of the excitation light in the direction of the molecular axis of the fluorescent probe (i.e., proportional to the square of the amplitude), and is thus expressed as follows.

$$p_{1p}(\alpha)=p_0^{1p} \cdot \cos^2 \alpha \qquad (44)$$

Here, $p_0^{1p}$ is the excitation probability of the fluorescent probe having the molecular axis along the direction (α=0) parallel to the polarized direction of the excitation light in the case of one-photon excitation. On the other hand, the excitation probability $p_{2p}$ in the case of two-photon excitation is proportional to the square of the intensity of the excitation light in the direction of the molecular axis of the fluorescent probe, and is thus expressed as follows.

$$p_{2p}(\alpha)=p_0^{2p} \cdot \cos^4 \alpha \qquad (45)$$

Here, $p_0^{2p}$ is the excitation probability of the fluorescent probe having the molecular axis along the direction (α=0) parallel to the polarized direction of the excitation light in the case of two-photon excitation.

Figure 21:
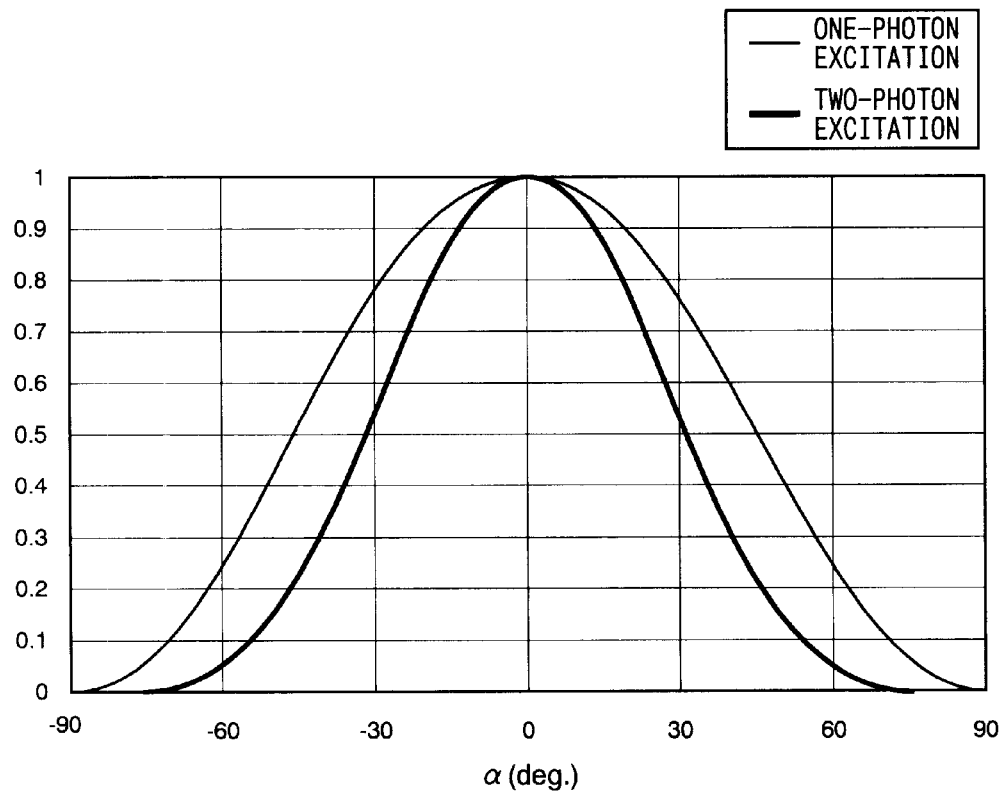
FIG. 21 is a graph to show excitation probabilities for each of the one-photon excitation case (thin line) and the two-photon excitation case (thick line).

FIG. 21 is a graph to show the excitation probabilities $p_{1p}(\alpha)$ in the case of one-photon excitation and the excitation probabilities $p_{2p}(\alpha)$ in the case of two-photon excitation. Here, each value of $p_0^{1p}$ and $p_0^{2p}$, which are the excitation probabilities at α=0, is normalized to 1. As illustrated in this figure, the excitation probabilities show quicker decrease with increasing absolute values of angle α in the case of two-photon excitation than in the case of one-photon excitation. Namely, the excitation probabilities of the fluorescent probe molecules having the molecular axes along directions (α≠0) different from the polarized direction of the excitation light with respect to the excitation probability of the fluorescent probe having the molecular axis along the direction (α=0) parallel to the polarized direction of the excitation light, are smaller in the case of two-photon excitation than in the case of one-photon excitation. Therefore, in the case where the polarization characteristic measurement is carried out in a system wherein directions of molecular axes of fluorescent probe molecules are oriented at random in a sample, the fluorescent probe molecules having the molecular axis parallel to the polarized direction of the excitation light are excited more selectively in the case of two-photon excitation than in the case of one-photon excitation.

Figure 22:
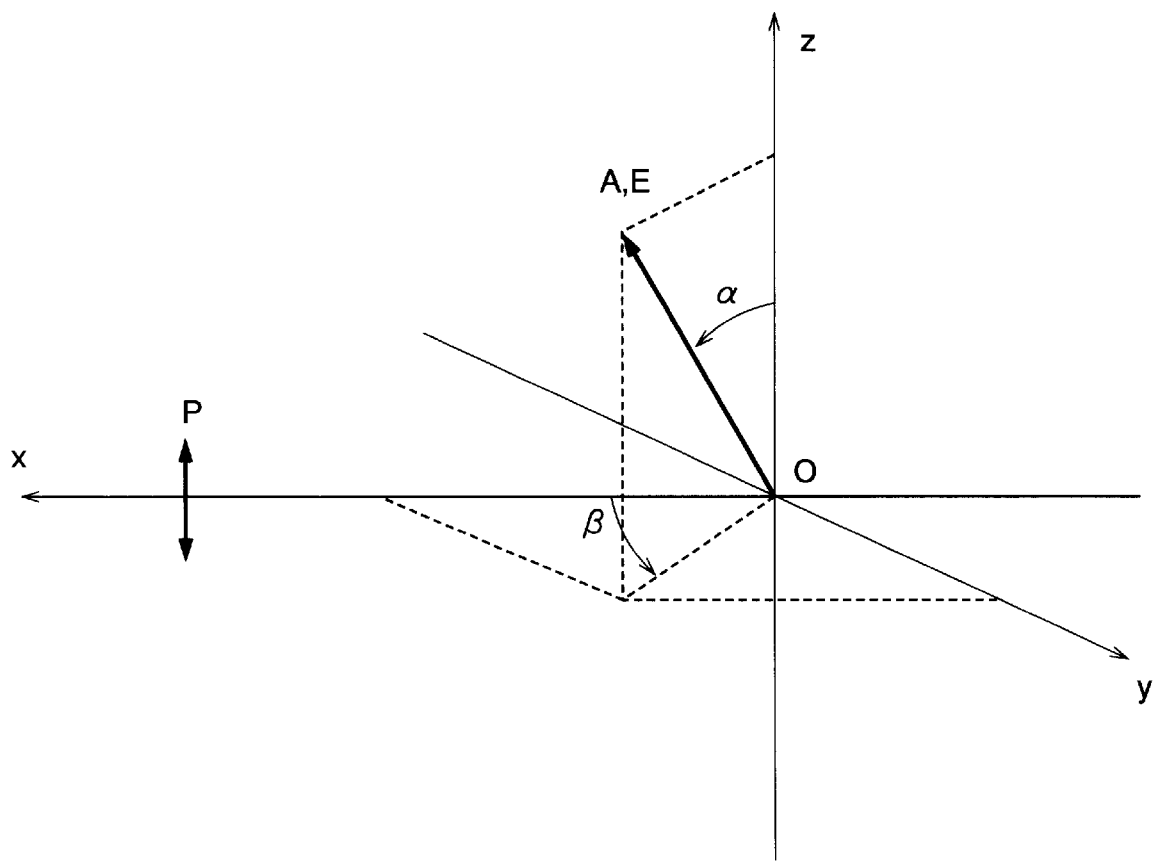
FIG. 22 is a drawing to explain the relation between a polarized direction of excitation light and a direction of molecular axis of fluorescent probe.

Next, let us obtain the anisotropy ratio $P_2$ of fluorescence emitted from the fluorescent probe excited in the above excitation probabilities, for each of the one-photon excitation case and the two-photon excitation case. FIG. 22 is a drawing to explain the relation between the polarized direction of the excitation light and the direction of molecular axis of the fluorescent probe. Let us set the xyz orthogonal coordinate system, where the x-direction is taken along the direction of propagation of the excitation light and the z-direction along the polarized direction P of the excitation light. The direction A of the molecular axis of the fluorescent probe and the polarized direction E of fluorescence coincide with each other and make the angle α with the z-axis. Projection of the direction A and E onto the xy-plane makes the angle β with the x-axis. It is also assumed that directions of molecular axes of fluorescent probe molecules are oriented at random.

In this case, defining k as the intensity of the fluorescence emitted from the fluorescent probe, the intensity $i_z$ of the component along the z-axis direction of the fluorescence, the intensity $i_x$ of the component along the x-axis direction thereof, and the intensity $i_y$ of the component along the y-axis direction thereof are expressed respectively by the following equations.

$$i_z = k \cdot \cos^2 \alpha \tag{46a}$$

$$i_x = k \cdot \sin^2 \alpha \cdot \cos^2 \beta \tag{46b}$$

$$i_y = k \cdot \sin^2 \alpha \cdot \sin^2 \beta \tag{46c}$$

the number of fluorescent probe molecules whose directions A of molecular axes are between $\alpha$ and $\alpha+d\alpha$ and between $\beta$ and $\beta+d\beta$, is proportional to the following.

$$\sin \alpha \cdot d\alpha \cdot d\beta \tag{47}$$

Therefore, from Eq. (44), Eq. (45), and Eq. (47), the number of fluorescent probe molecules whose directions A of molecular axes (i.e., polarized directions E of fluorescence) are between $\alpha$ and $\alpha+d\alpha$ and between $\beta$ and $\beta+d\beta$, out of the fluorescent probe molecules excited with the excitation light, is proportional to Eq. (48) below in the case of one-photon excitation; or it is proportional to Eq. (49) below in the case of two-photon excitation.

$$\cos^2 \alpha \cdot \sin \alpha \cdot d\alpha \cdot d\beta \equiv \Omega_{1p}(\alpha) \cdot d\alpha \cdot d\beta \tag{48}$$

$$\cos^4 \alpha \cdot \sin \alpha \cdot d\alpha \cdot d\beta \equiv \Omega_{2p}(\alpha) \cdot d\alpha \cdot d\beta \tag{49}$$

In general, when $\Omega(\alpha)$ represents a distribution of fluorescent probe molecules whose directions A of molecular axes have angles $\alpha$ relative to the z-axis out of the fluorescent probe molecules excited by irradiation with the excitation light, the intensity $I_z$ of the component along the z-axis direction, the intensity $I_x$ of the component along the x-axis direction, and the intensity $I_y$ of the component along the y-axis direction of the fluorescence emitted from the sample, which is a population of fluorescent probe molecules, are expressed as follows from Eqs. (46a), (46b), and (46c), respectively; and in that case, the relation (51) holds.

$$I_z = K \cdot \frac{\int_0^{\pi/2} \cos^2 \alpha \cdot \Omega(\alpha) \cdot d\alpha}{\int_0^{\pi/2} \Omega(\alpha) \cdot d\alpha} \tag{50a}$$

$$I_x = \frac{K}{2} \cdot \frac{\int_0^{\pi/2} \sin^2 \alpha \cdot \Omega(\alpha) \cdot d\alpha}{\int_0^{\pi/2} \Omega(\alpha) \cdot d\alpha} \tag{50b}$$

$$I_y = \frac{K}{2} \cdot \frac{\int_0^{\pi/2} \sin^2 \alpha \cdot \Omega(\alpha) \cdot d\alpha}{\int_0^{\pi/2} \Omega(\alpha) \cdot d\alpha} \tag{50c}$$

$$I_z \neq I_x = I_y \tag{51}$$

Here, K is a proportional constant.

Further, in general, the anisotropy ratio $P_2$ of fluorescence is given by dividing a difference between the intensity $I_z$ of the fluorescence polarized component parallel to the polarized direction of the excitation light and the intensity $I_x$ or $I_y$ of the fluorescence polarized component perpendicular to the polarized direction of the excitation light by the total fluorescence amount $I_x+I_y+I_z$ as follows.

$$P_2 = (I_z - I_x)/(I_z + 2I_x) \tag{52}$$

Substituting Eqs. (50a), (50b), (50c) into this Eq. (52), the following equation is obtained.

$$P_2 = (3 \cdot \langle \cos^2 \alpha \rangle - 1)/2 \tag{53}$$

Here, $\langle \cos^2 \alpha \rangle$ is as follows.

$$\langle \cos^2 \alpha \rangle = \frac{\int_0^{\pi/2} \cos^2 \alpha \cdot \Omega(\alpha) \cdot d\alpha}{\int_0^{\pi/2} \Omega(\alpha) \cdot d\alpha} \tag{54}$$

From the above discussion, in the case of one-photon excitation, the value of the anisotropy ratio $P_2^{1p}(0)$ of the fluorescence immediately after excitation (i.e., before it is depolarized because of the rotational Brownian motion of fluorescent probe) is obtained by substituting $\Omega_{1p}(\alpha)$ Eq. (48) into $\Omega(\alpha)$ of Eq. (54) and by calculating Eq. (53) as follows.

$$P_2^{1p}(0) = 2/5 = 0.4 \tag{55}$$

On the other hand, in the case of two-photon excitation, the value of the anisotropy ratio $P_2^{2p}(0)$ of fluorescence immediately after excitation is obtained by substituting $\Omega_{2p}(\alpha)$ of Eq. (49) into $\Omega(\alpha)$ of Eq. (54) and by calculating Eq. (53) as follows.

$$P_2^{2p}(0) = 4/7 \approx 0.57 \tag{56}$$

As described above, the initial value $P_2(0)$ of the anisotropy ratio of fluorescence in the two-photon excitation case is 1.43 (=0.57/0.4) times greater than in the one-photon excitation case. When the fluorescent probe molecules excited are under the rotational Brownian motion, values of anisotropy ratio $P_2$ of fluorescence emitted from the fluorescent probe gradually decrease from the initial value given by above Eq. (55) or Eq. (56). Thus, the dynamic range of polarization characteristic measurement in the two-photon excitation case is 1.43 times wider than in the one-photon excitation case. This is also the case in the excitation with steady-state light.

Next, let us examine the sensitivity of polarization characteristic measurement in each of the one-photon excitation case and the two-photon excitation case. A ratio of the intensity $I_s$ (=$I_y$) of the fluorescence polarized component perpendicular to the polarized direction of the excitation light to the intensity $I_p$(=$I_z$) of the fluorescence polarized component parallel to the polarized direction of the excitation light immediately after the excitation is expressed as follows from Eqs. (50a), (50b), and (50c).

$$\frac{I_s}{I_p} = \frac{\int_0^{\pi/2} \sin^2 \alpha \cdot \Omega(\alpha) \cdot d\alpha}{2 \cdot \int_0^{\pi/2} \cos^2 \alpha \cdot \Omega(\alpha) \cdot d\alpha} \tag{57}$$

In the one-photon excitation case, by substituting $\Omega_{1p}(\alpha)$ of Eq. (48) into $\Omega(\alpha)$ of Eq. (57), the following ratio is obtained.

$$I_s/I_p = 1/3 \tag{58}$$

In the two-photon excitation case, by substituting $\Omega_{2p}(\alpha)$ of Eq. (49) into $\Omega(\alpha)$ of Eq. (57), the following ratio is obtained.

$$I_s/I_p = 1/5 \quad (59)$$

Therefore, because of the rotational Brownian motion of the fluorescent probe molecules excited, the ratio $I_s/I_p$ varies from 1/3 to 1 in the one-photon excitation case, whereas it varies from 1/5 to 1 in the two-photon excitation case. Therefore, the sensitivity of polarization characteristic measurement is higher in the case of the two-photon excitation than in the case of the one-photon excitation.

Next, let us examine the measurement sensitivity of polarization characteristic of fluorescence emitted from fluorescent probe molecules continuously excited at constant intensity, for each of the one-photon excitation case and the two-photon excitation case. When the fluorescence lifetime is $\tau$, the rotational correlation time of fluorescent probe is $\theta$, and the maximum of the anisotropy ratio of fluorescence (which is the value given by Eq. (55) or Eq. (56)) is $P_2(0)$, the anisotropy ratio $P_2$ of fluorescence is expressed by the following equation.

$$P_2 = \frac{P_2(0)}{1+\tau/\theta} \quad (60)$$

Here, the rotational correlation time $\theta$ is the quantity featuring the speed of rotational Brownian motion of fluorescent probe and the fluorescent probe bound to the target and the fluorescent probe in the free state have different values of rotational correlation time. When the fluorescent probe molecules are spherical particles, the rotational correlation time $\theta$ is given by the following equation where the volume of fluorescent probe molecule is V, the absolute temperature of solvent is T, the viscosity of solvent is $\eta$, and the Boltzmann constant is k.

$$\frac{1}{\theta} = \frac{k \cdot T}{V \cdot \eta} \quad (61)$$

Figure 23:
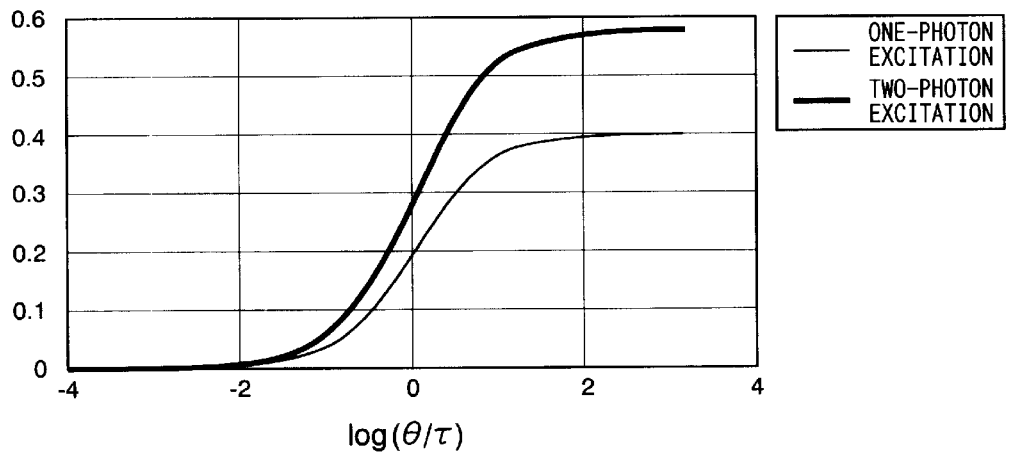
FIG. 23 is a graph to show plots of values of anisotropy ratio $P_2$ of fluorescence as a function of $\theta/\tau$ in the case of excitation with steady-state light, for each of the one-photon excitation case (thin line) and the two-photon excitation case (thick line).
Figure 24:
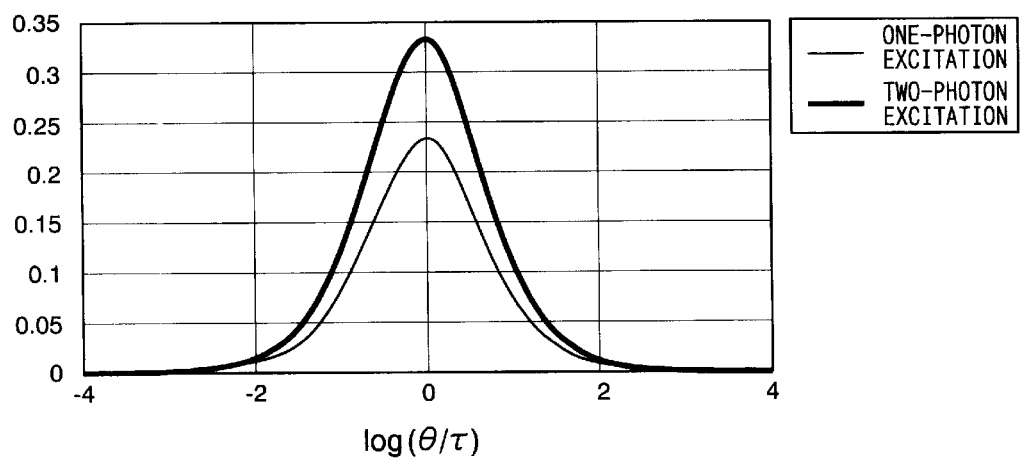
FIG. 24 is a graph to show plots of gradient of anisotropy ratio $P_2$ of fluorescence as a function of $\theta/96$ in the case of excitation with steady-state light, for each of the one-photon excitation case (thin line) and the two-photon excitation case (thick line).

FIG. 23 is a graph to show plots of values of anisotropy ratio $P_2$ (Eq. (60)) of fluorescence as a function of $\theta/\tau$ in the case of excitation with steady-state light, for each of the one-photon excitation case (thin line) and the two-photon excitation case (thick line). FIG. 24 is a graph to show plots of gradients of the anisotropy ratio $P_2$ (Eq. (60)) of fluorescence with respect to $\theta/\tau$ in the case of excitation with steady-state light, for each of the one-photon excitation case (thin line) and the two-photon excitation case (thick line). As seen from these figures, the values of anisotropy ratio $P_2$ of fluorescence and the gradients of anisotropy ratio $P_2$ of fluorescence with respect to $\theta/\tau$ are greater in the two-photon excitation case (thick line) than in the one-photon excitation case (thin line). Therefore, the anisotropy ratio $P_2$ of fluorescence is more sensitive to change in $\theta/\tau$ in the two-photon excitation case than in the one-photon excitation case.

Differentiating Eq. (60) above with respect to $\theta$, the following equation is attained.

$$\frac{dP_2}{d\theta} = P_2(0)\frac{\tau}{(\theta+\tau)^2} \quad (62)$$

Supposing the fluorescence lifetime $\tau$ is constant in the one-photon excitation case and in the two-photon excitation case, the following relation holds from Eq. (55) and Eq. (56).

$$P_2^{2p}(0) > P_2^{1p}(0) \quad (63)$$

Therefore, the following relation results.

$$\frac{dP_2^{2p}}{d\theta} > \frac{dP_2^{1p}}{d\theta} \quad (64)$$

Namely, the anisotropy ratio $P_2$ of fluorescence is more sensitive to change in the rotational correlation time $\theta$ in the two-photon excitation case than in the one-photon excitation case.

Next, let us examine the S/N ratio of measured value of polarization characteristic of fluorescence, for each of the one-photon excitation case and the two-photon excitation case. Let us indicate the mean value of anisotropy ratio $P_2$ of fluorescence as $<P_2>$, the standard deviation of anisotropy ratio $P_2$ as $\sigma$, the number of incident photons of the fluorescence polarized component parallel to the polarized direction of excitation light into the photodetector as $<n_p>$, the number of incident photons of the fluorescence polarized component perpendicular to the polarized direction of excitation light into the photodetector as $<n_s>$, and the quantum efficiency of the photocathode of the photodetector as $\epsilon$. Then the S/N ratio of measured value of polarization characteristic of fluorescence is given by the following equation.

$$\frac{S}{N} \equiv \frac{\langle P_2 \rangle}{\sigma} \approx \langle P_2 \rangle \cdot [\varepsilon \cdot (\langle n_p \rangle + \langle n_s \rangle)]^{1/2} \quad (65)$$

In the case of the excitation with steady-state light, the following relation holds.

$$\langle P_2 \rangle = \frac{P_2(0)}{1+\tau/\theta} \quad (66)$$

Thus, Eq. (65) becomes as follows.

$$\frac{S}{N} = \frac{P_2(0)}{1+\tau/\theta} \cdot [\varepsilon \cdot (\langle n_p \rangle + \langle n_s \rangle)]^{1/2} \quad (67)$$

If the number of photons of fluorescence in the two-photon excitation case is equal to that in the one-photon excitation case, the S/N ratio in the two-photon excitation case is 1.43 times greater than in the one-photon excitation case. A ratio of numbers of photons necessary for achieving an identical S/N ratio for an identical value of $\tau/\theta$ in the one-photon excitation case and in the two-photon excitation case is as follows.

$$\frac{(\langle n_p \rangle + \langle n_s \rangle)_{2p}}{(\langle n_p \rangle + \langle n_s \rangle)_{1p}} = \left(P_2^{1p}(0)/P_2^{2p}(0)\right)^2 \approx 1/2 \quad (68)$$

Namely, the number of photons necessary for achieving the same S/N ratio for the same value of $\tau/\theta$ in the two-photon excitation case is a half of that in the one-photon excitation case.

Next, let us examine the detection limit of rotational correlation time $\theta$ of fluorescent probe when the standard deviation (noise) $\sigma$ of measured value of polarization characteristic is given, for each of the one-photon excitation case and the two-photon excitation case. Let us define the mean anisotropy ratio against the value $\theta$ of rotational correlation time as $<P_2(\theta)>$, the mean anisotropy ratio against value $\theta+\Delta\theta$ of rotational correlation time as $<P_2(\theta+\Delta\theta)>$, and the detection limit of rotational correlation time θ as Δθ. Then the following relation holds.

$$\langle P_2(\theta + \Delta\theta)\rangle - \langle P_2(\theta)\rangle = \sigma \quad (69)$$

From this, the following is obtained as an equation representing the detection limit Δθ of the rotational correlation time θ.

$$\Delta\theta = \frac{(\theta + \tau)^2}{(P_2(0)/\sigma)\tau - (\theta + \tau)} \quad (70)$$

From Eq. (63) and Eq. (70), the detection limit Δθ of the rotational correlation time θ is higher in the two-photon excitation case than in the one-photon excitation case under the same noise condition.

The above description concerned the one-photon excitation case and the two-photon excitation case for the anisotropy ratio $P_2$ of fluorescence, but similar discussion can be made for the other polarization characteristics ($P_1$, $P_3$, $P_4$). In the case of the two-photon excitation the two-dimensional image of polarization characteristic of fluorescence can also be measured with high accuracy under the microscope by effecting the polarization response correction based on the G factor in the same manner as in the case of the one-photon excitation. In the case of the two-photon excitation, in addition to it, because the fluorescent probe molecules having the molecular axis parallel to the polarized direction of excitation light are excited selectively, the more excellent effects than in the one-photon excitation case are achieved; the initial values of polarization characteristics ($P_1$, $P_2$, $P_3$, $P_4$) are large, the dynamic range of measurement of polarization characteristic is wide, the sensitivity of measurement of polarization characteristic to the rotational correlation time θ is high, the S/N ratio of measured value of polarization characteristic is high, the number of photons necessary for obtaining the same S/N ratio is small, and the detection limit Δθ of the rotational correlation time θ is high.

In order to examine the above theory, the following experiments were conducted. The fluorescent probe was BODIPY dye and the sample was a solution obtained by dissolving this BODIPY dye in a solution containing ethanol and glycerol. Adjustment of the rotational correlation time θ or the speed of rotational Brownian motion of this fluorescent probe was made by adjusting the viscosity η of the solution, i.e., by adjusting the rate of glycerol. The speed of the rotational Brownian motion is inversely proportional to the viscosity η of the solution.

The polarization characteristic measuring apparatus used herein had the structure shown in FIG. 10 and the measurement of polarization characteristic was conducted under the microscope. The pulsed excitation light source 1 was a mode-locked Ti:sapphire laser light source; in the two-photon excitation case, laser light (the wavelength 920 nm, the pulsewidth 200 fsec, the repetition rate 76 MHz) radiated from this laser source was used as the excitation light; in the one-photon excitation case, the second harmonic thereof (the wavelength 460 nm, the repetition rate 100 kHz) was used as the excitation light. The objective lens 6 was one having the magnification of 20×. The gated image intensifiers 13, 14 were used in such a state that the gates thereof were always open.

Figure 26:
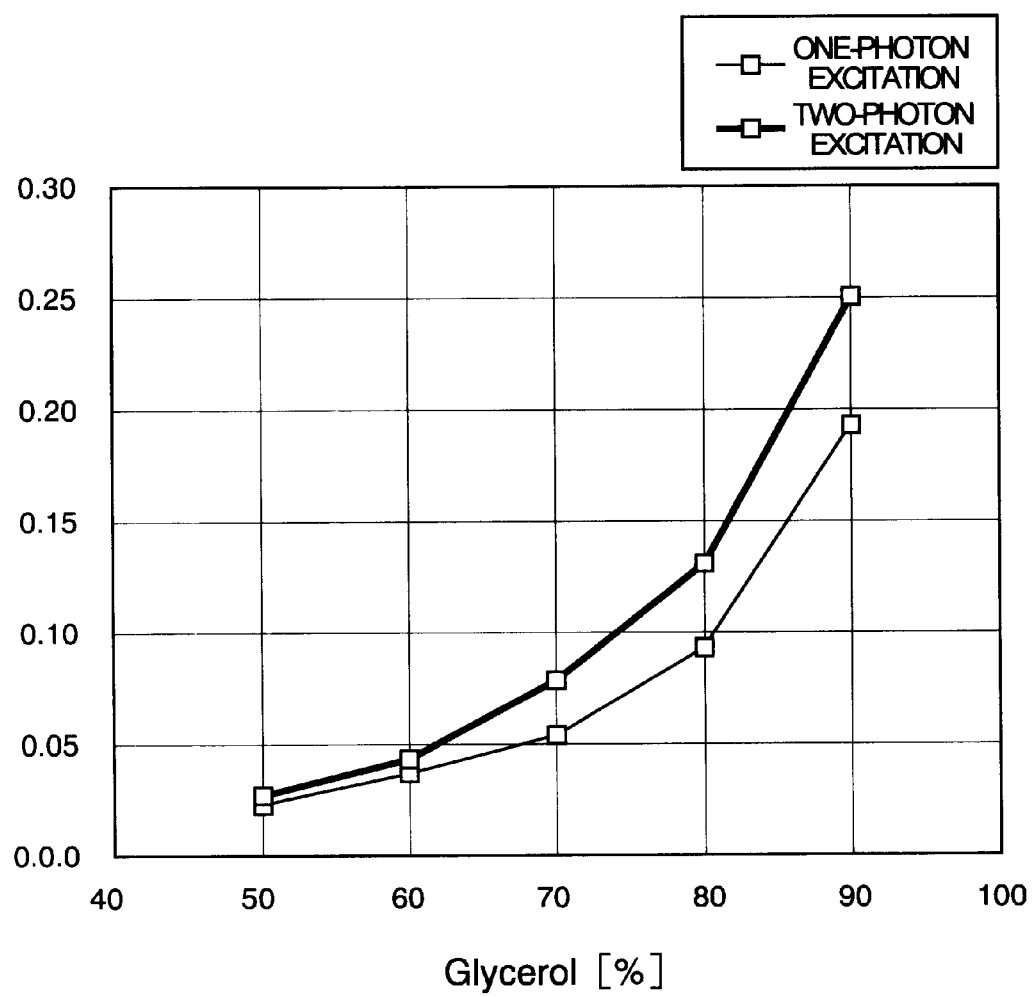
FIG. 26 is a graph to show plots of measured values of anisotropy ratio $P_2$ of fluorescence against glycerol percentage, for each of the one-photon excitation case (thin line) and the two-photon excitation case (thick line).

FIG. 25 is a table to show measured values of anisotropy ratio $P_2$ and standard deviation σ of fluorescence against glycerol percentage, for each of the one-photon excitation case and the two-photon excitation case. FIG. 26 is a graph to show plots of measured values of anisotropy ratio $P_2$ of fluorescence against glycerol percentage, for each of the one-photon excitation case (thin line) and the two-photon excitation case (thick line). As seen from these figures, the anisotropy ratios $P_2$ of fluorescence increase with increasing glycerol percentages, i.e., with increasing viscosity η of solution and increasing rotational correlation time θ, in either of the one-photon excitation case and the two-photon excitation case. The anisotropy ratios $P_2$ of fluorescence are larger in the two-photon excitation case than in the one-photon excitation case. These agree with the theory discussed above. Further, ratios of anisotropy ratio $P_2$ of fluorescence in the two-photon excitation case to that in the one-photon excitation case were 1.15 at the glycerol percentage of 50%, 1.19 at 60%, 1.41 at 70%, 1.40 at 80%, and 1.31 at 90%; therefore, the ratios at the glycerol percentages of 70% and 80% are close to the theoretical value 1.43.

Figure 28:
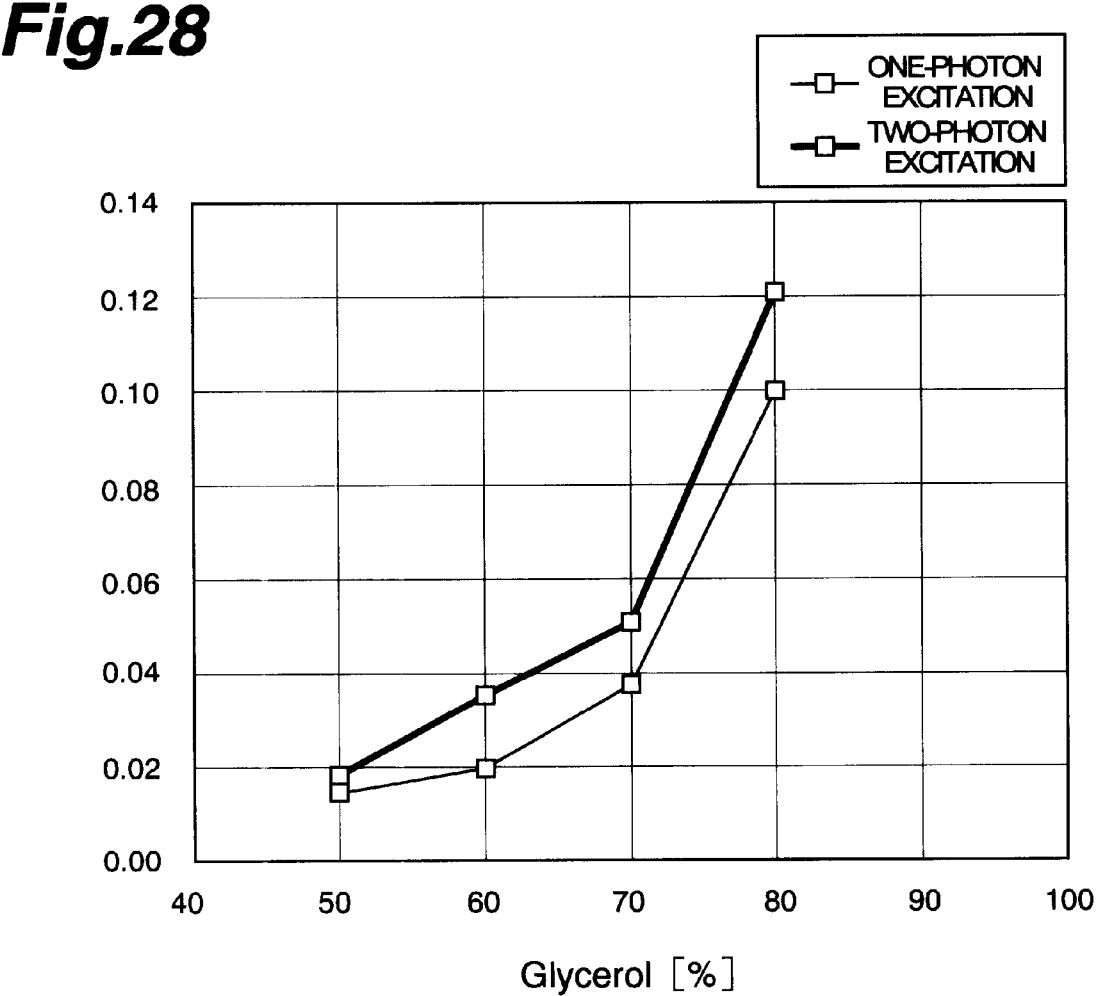
FIG. 28 is a graph to show plots of values of increment $\Delta P_2$ of anisotropy ratio $P_2$ of fluorescence against 10%-interval increase of glycerol percentage, for each of the one-photon excitation case (thin line) and the two-photon excitation case (thick line).

FIG. 27 is a table to show increments $\Delta P_2$ of anisotropy ratio $P_2$ of fluorescence against 10% increase of glycerol percentage, for each of the one-photon excitation case and the two-photon excitation case. FIG. 28 is a graph to show plots of values of increment $\Delta P_2$ of anisotropy ratio $P_2$ of fluorescence against 10% increase of glycerol percentage, for each of the one-photon excitation case (thin line) and the two-photon excitation case (thick line). As apparent from these figures, the increments $\Delta P_2$ of the anisotropy ratio $P_2$ of fluorescence are larger in the two-photon excitation case than in the one-photon excitation case. These agree with the theory discussed above. Further, the mean of ratios of increment $\Delta P_2$ of the anisotropy ratio $P_2$ of fluorescence in the two-photon excitation case to that in the one-photon excitation case was 1.42 and it is thus close to the theoretical value 1.43.

Figure 30:
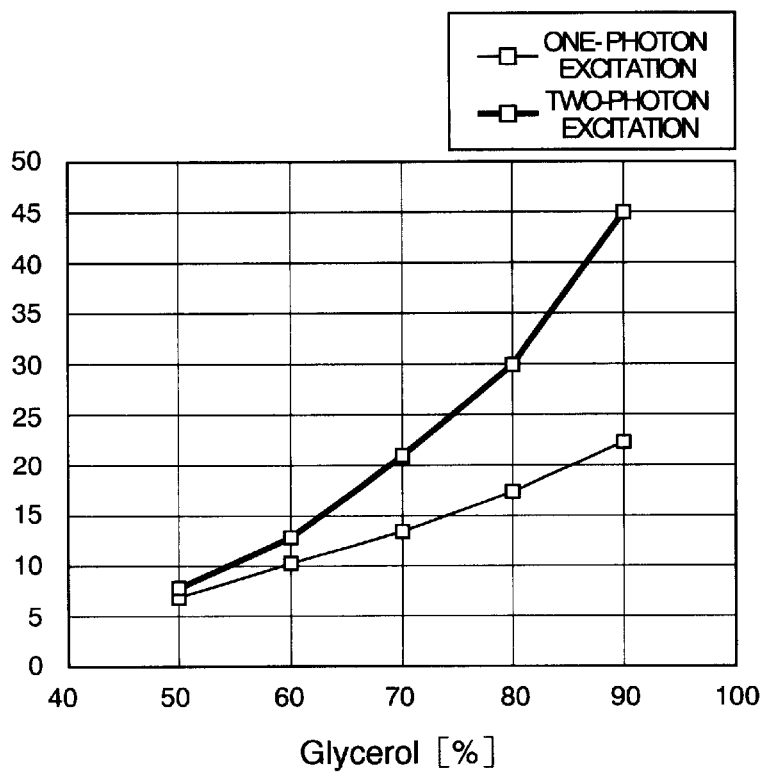
FIG. 30 is a graph to show plots of values ($P_2/\sigma$) obtained by dividing the anisotropy ratio $P_2$ of fluorescence by the standard deviation $\sigma$, against glycerol percentage, for each of the one-photon excitation case (thin line) and the two-photon excitation case (thick line).
Figure 31:
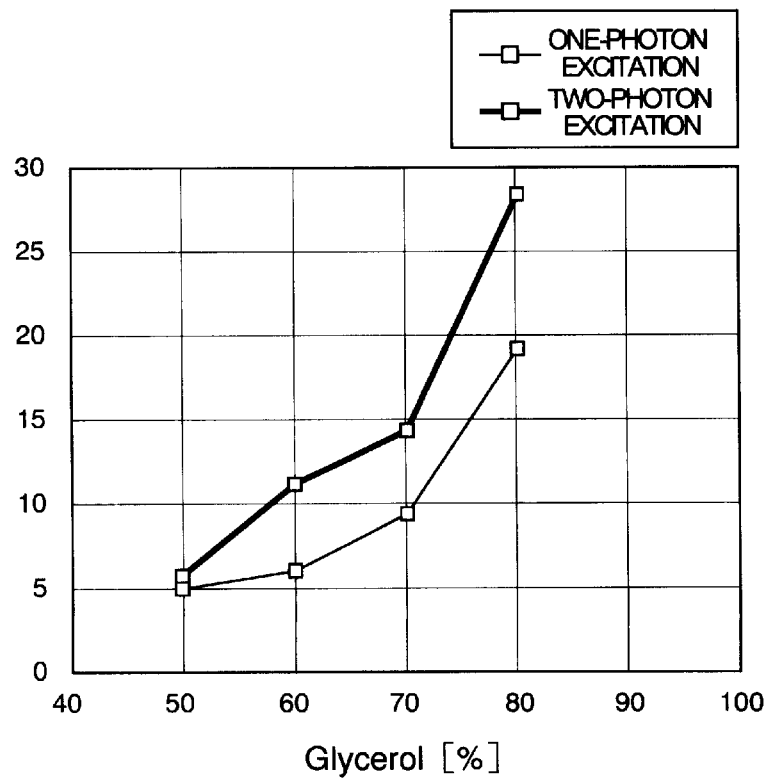
FIG. 31 is a graph to show plots of values ($\Delta P_2/\sigma$) obtained by dividing the increment $\Delta P_2$ of the anisotropy ratio $P_2$ of fluorescence by the standard deviation $\sigma$, against glycerol percentage, for each of the one-photon excitation case (thin line) and the two-photon excitation case (thick line).

FIG. 29 is a table to show values obtained by dividing the anisotropy ratio $P_2$ of fluorescence by the standard deviation σ ($P_2/\sigma$) and values obtained by dividing the increment $\Delta P_2$ of anisotropy ratio $P_2$ of fluorescence by the standard deviation σ ($\Delta P_2/\sigma$), each against glycerol percentage, for each of the one-photon excitation case and the two-photon excitation case. FIG. 30 is a graph to show plots of values ($P_2/\sigma$) obtained by dividing the anisotropy ratio $P_2$ of fluorescence by the standard deviation σ, against glycerol percentage, for each of the one-photon excitation case (thin line) and the two-photon excitation case (thick line). FIG. 31 is a graph to show plots of values ($\Delta P_2/\sigma$) obtained by dividing the increment $\Delta P_2$ of anisotropy ratio $P_2$ of fluorescence by the standard deviation a, against glycerol percentage, for each of the one-photon excitation case (thin line) and the two-photon excitation case (thick line). As seen from these figures, the S/N ratios (=$P_2/\sigma$) and the detection limit Δθ (=$\Delta P_2/\sigma$) of the rotational correlation time θ both are higher in the two-photon excitation case than in the one-photon excitation case.

Next described is the structure of the polarization characteristic measuring apparatus that can be suitably used in the two-photon excitation case.

The polarization characteristic measuring apparatus of the structure shown in FIG. 10 can also be used in the two-photon excitation case. As discussed in the above theory and experiment results, the polarization characteristic measurement of fluorescence emitted from the fluorescent probe in the sample excited by two-photon excitation has the excellent effects, but the excitation light needs to be very strong in the two-photon excitation case; in order to achieve the intensity of fluorescence equivalent to that in the one-photon excitation case, the intensity of excitation light needs to be approximately 100 times that in the one-photon excitation case. In the structure shown in FIG. 10, therefore, the excitation light reflected or scattered by the sample 7, transmitted by the dichroic mirror 5, and reaching the gated image intensifiers 13, 14 is stronger than in the one-photon excitation case and is sometimes not negligible. It is thus preferred to additionally interpose a filter for intercepting the excitation light, on the optical path between the dichroic mirror 5 and each of the gated image intensifiers 13, 14, in addition to the structure shown in FIG. 10.

More preferably, the polarization characteristic measuring apparatus having the detection optical system shown in FIG. 20A and FIG. 20B can be employed in the two-photon excitation case. Specifically, the dichroic mirror 17 functions to cancel the polarization characteristics of the dichroic mirror 5 and also functions as a filter for intercepting the strong reflected and scattered light of the excitation light, thereby improving the S/N ratio of measurement of polarization.

As detailed above, the polarization characteristic measuring method and apparatus according to the present invention can obtain the two-dimensional image of polarization characteristic ($P_1$, $P_2$, $P_3$, $P_4$) of fluorescence emitted from the sample including the fluorescent probe under the microscope. In addition, the high-accuracy measurement of polarization characteristic can also be performed by effecting the polarization response correction under the microscope such as the polarization characteristic measuring apparatus according to the present invention.

The measurement of polarization characteristic was described with the examples of imaging of depolarization in the above description of the embodiments, but the present invention is not limited to only the two dimensions (imaging); the present invention can also be applied to measurements of polarization characteristic of dimension 0 (point) and dimension 1. The present invention is not limited to only the measurement of depolarization, either. The invention was described as to the measurement of polarization characteristic of fluorescence emitted when the sample was exposed to the excitation light, but the same is also applicable to the measurement of polarization characteristic of Raman-scattered light.

Industrial Applicability

As detailed above, the polarization characteristic measuring method and apparatus according to the present invention can measure the two-dimensional image of polarization characteristic of the second beam (fluorescence or Raman-scattered light) emitted when the sample is exposed to the first beam (excitation light or irradiating light), under the microscope. Therefore, for example, when the present invention is applied to imaging of fluorescence depolarization, the position where the fluorescent probe bound to the target exists can be specified with high accuracy and thus the behavior or the like of the target in the sample can be analyzed; therefore, the invention can contribute, for example, to elucidation of various functions in cells.

We claim:

1. A polarization characteristic measuring method using beam splitting means for reflecting one of a first beam for irradiation of a sample and a second beam emitted from said sample and for transmitting the other, said polarization characteristic measuring method being adapted for guiding said first beam via said beam splitting means onto said sample, thereby effecting irradiation of the sample, and for measuring a polarization characteristic of said second beam emitted from said sample under the irradiation and traveling via said beam splitting means, said polarization characteristic measuring method comprising:

a first step of measuring an intensity $I_{pp}$ of a p-polarized component and an intensity $I_{ps}$ of an s-polarized component of said second beam emitted when said sample is irradiated with said first beam in the form of p-polarized light with respect to said beam splitting means;

a second step of measuring an intensity $I_{sp}$ of a p-polarized component and an intensity $I_{ss}$ of an s-polarized component of said second beam emitted when said sample is irradiated with said first beam in the form of s-polarized light with respect to said beam splitting means;

a third step of calculating a polarization response correction factor G according to the following equation:

$$G=[(I_{pp} \cdot I_{sp})/(I_{ps} \cdot I_{ss})]^{1/2}; \text{ and}$$

a fourth step of performing polarization response correction based on said polarization response correction factor G to obtain the polarization characteristic of said second beam.

2. The polarization characteristic measuring method according to claim 1, wherein said second step comprises a step of radiating said first beam toward said sample set in the same location as during measurement of said first step.

3. The polarization characteristic measuring method according to claim 1, wherein said first step comprises a step of radiating said first beam toward said sample located at a position making a predetermined rotation angle about a center axis on a predetermined direction, and wherein said second step comprises a step of radiating said first beam toward said sample located at a position making a rotation angle 90° different from said position of the predetermined rotation angle about said center axis.

4. The polarization characteristic measuring method according to claim 1, wherein said fourth step comprises a step of obtaining a polarization characteristic P of said second beam according to either equation below:

$$P_1(p)=(I_{pp}-G \cdot I_{ps})/(I_{pp}+G \cdot I_{ps}); \text{ or}$$

$$P_1(s)=(G \cdot I_{ss}-I_{sp})/(G \cdot I_{ss}+I_{sp}).$$

5. The polarization characteristic measuring method according to claim 1, wherein said fourth step comprises a step of obtaining a polarization characteristic P of said second beam according to either equation below:

$$P_2(p)=(I_{pp}-G \cdot I_{ps})/(I_{pp}+2 \cdot G \cdot I_{ps}); \text{ or}$$

$$P_2(s)=(G \cdot I_{ss}-I_{sp})/(G \cdot I_{ss}+2 \cdot I_{sp}).$$

6. The polarization characteristic measuring method according to claim 1, wherein said fourth step comprises a step of obtaining a polarization characteristic P of said second beam according to either equation below:

$$P_3(p)=1-G \cdot (I_{ps}/I_{pp}); \text{ or}$$

$$P_3(s)=G-(I_{sp}/I_{ss}).$$

7. The polarization characteristic measuring method according to claim 1, wherein said fourth step comprises a step of obtaining a polarization characteristic P of said second beam according to either equation below:

$$P_4(p)=(I_{pp}/I_{ps})-G; \text{ or}$$

$$P_4(s)=G\cdot(I_{ss}/I_{sp})-1.$$

8. The polarization characteristic measuring method according to claim 1, wherein said first beam is a beam of a wavelength that can undergo multiple photon absorption by said sample and said second beam is a beam emitted on the occasion of said multiple photon absorption.

9. A polarization characteristic measuring apparatus using beam splitting means for reflecting one of a first beam for irradiation of a sample and a second beam emitted from said sample and for transmitting the other, said polarization characteristic measuring apparatus being adapted for guiding said first beam via said beam splitting means onto said sample, thereby effecting irradiation of the sample, and for measuring a polarization characteristic of said second beam emitted from said sample under the irradiation and traveling via said beam splitting means, said polarization characteristic measuring apparatus comprising:

a light source portion for outputting the first beam of linearly polarized light for irradiation of the sample;

polarized direction rotating means for rotating a polarized direction of said first beam outputted from said light source portion;

detecting means for detecting intensities of respective p-polarized component and s-polarized component of said second beam traveling via said beam splitting means, out of beams emitted when said sample is irradiated with said first beam;

correction factor calculating means for calculating a polarization response correction factor G according to the following equation:

$$G=[(I_{pp}\cdot I_{sp})/(I_{ps}\cdot I_{ss})]^{1/2},$$

based on an intensity $I_{pp}$ of a p-polarized component and an intensity $I_{ps}$ of an s-polarized component of said second beam detected by said detecting means when said sample is irradiated with said first beam changed to p-polarized light with respect to said beam splitting means by said polarized direction rotating means and on an intensity $I_{sp}$ of a p-polarized component and an intensity $I_{ss}$ of an s-polarized component of said second beam detected by said detecting means when said sample is irradiated with said first beam changed to s-polarized light with respect to said beam splitting means by said polarized direction rotating means; and polarization characteristic calculating means for performing polarization response correction based on said polarization response correction factor G to obtain a polarization characteristic of said second beam.

10. The polarization characteristic measuring apparatus according to claim 9, wherein said correction factor calculating means calculates said polarization response correction factor G, based on said intensities $I_{pp}$, $I_{ps}$, $I_{sp}$, and $I_{ss}$ detected by said detecting means, for said sample located in a fixed location.

11. The polarization characteristic measuring apparatus according to claim 9, further comprising sample rotating means for rotating said sample about a center axis on a predetermined direction, wherein said correction factor calculating means calculates said polarization response correction factor G. based on said intensities $I_{pp}$ and $I_{ps}$ detected by said detecting means, for said sample located at a position making a predetermined rotation angle about said center axis and on said intensities $I_{sp}$ and $I_{ss}$ detected by said detecting means, for said sample set at a position making a rotation angle 90° different from said position of the predetermined rotation angle about said center axis by said sample rotating means.

12. The polarization characteristic measuring apparatus according to claim 9, wherein said polarization characteristic calculating means calculates a polarization characteristic P of said second beam according to either equation below:

$$P_1(p)=(I_{pp}-G\cdot I_{ps})/(I_{pp}+G\cdot I_{ps}); \text{ or}$$

$$P_1(s)=(G\cdot I_{ss}-I_{sp})/(G\cdot I_{ss}+I_{sp}).$$

13. The polarization characteristic measuring apparatus according to claim 9, wherein said polarization characteristic calculating means calculates a polarization characteristic P of said second beam according to either equation below:

$$P_2(p)=(I_{pp}-G\cdot I_{ps})/(I_{pp}+2\cdot G\cdot I_{ps}); \text{ or}$$

$$P_2(s)=(G\cdot I_{ss}-I_{sp})/(G\cdot I_{ss}+2\cdot I_{sp}).$$

14. The polarization characteristic measuring apparatus according to claim 9, wherein said polarization characteristic calculating means calculates a polarization characteristic P of said second beam according to either equation below:

$$P_3(p)=1-G\cdot(I_{ps}/I_{pp}); \text{ or}$$

$$P_3(s)=G-(I_{sp}/I_{ss}).$$

15. The polarization characteristic measuring apparatus according to claim 9, wherein said polarization characteristic calculating means calculates a polarization characteristic P of said second beam according to either equation below:

$$P_4(p)=(I_{pp}/I_{ps})-G; \text{ or}$$

$$P_4(s)=G\cdot(I_{ss}/I_{sp})-1.$$

16. The polarization characteristic measuring apparatus according to claim 9, wherein said light source portion outputs as said first beam a beam of a wavelength that can undergo multiple photon absorption by said sample, and said detecting means detects as said second beam a beam emitted on the occasion of said multiple photon absorption.

17. A polarization characteristic measuring apparatus comprising:

a light source portion for outputting a first beam for irradiation of a sample;

first beam splitting means for guiding said first bean onto said sample to effect irradiation of said sample and receiving a second beam emitted from said sample under the irradiation, said first beam splitting means reflecting one of said first beam and said second beam but transmitting the other;

second beam splitting means having a spectral characteristic equal to that of said first beam splitting means, said second beam splitting means having an plane of incidence 90° different from an plane of incidence of said first beam splitting means for said second beam, said second beam splitting means receiving said second beam outputted from said first beam splitting means;

detecting means for detecting intensities of respective p-polarized component and s-polarized component of said second beam traveling via said second beam splitting means; and polarization characteristic calculating means for measuring a polarization characteristic of said second beam, based on the intensities of the respective p-polarized component and s-polarized component of said second beam detected by said detecting means.

* * * * *